(12) United States Patent
Girouard

(10) Patent No.: US 10,226,209 B2
(45) Date of Patent: Mar. 12, 2019

(54) METHOD AND APPARATUS FOR CLASSIFICATION OF SEIZURE TYPE AND SEVERITY USING ELECTROMYOGRAPHY

(71) Applicant: Brain Sentinel, Inc., San Antonio, TX (US)

(72) Inventor: Michael R. Girouard, Shavano Park, TX (US)

(73) Assignee: Brain Sentinel, Inc., San Antonio, TX (US)

( * ) Notice: Subject to any disclaimer, the term of this patent is extended or adjusted under 35 U.S.C. 154(b) by 159 days.

(21) Appl. No.: 15/100,741

(22) PCT Filed: Dec. 2, 2014

(86) PCT No.: PCT/US2014/068246
§ 371 (c)(1),
(2) Date: Jun. 1, 2016

(87) PCT Pub. No.: WO2015/084899
PCT Pub. Date: Jun. 11, 2015

(65) Prior Publication Data
US 2016/0296157 A1    Oct. 13, 2016

Related U.S. Application Data

(63) Continuation-in-part of application No. 13/542,596, filed on Jul. 5, 2012, now Pat. No. 9,186,105, and a
(Continued)

(51) Int. Cl.
*A61B 5/04*    (2006.01)
*A61B 5/00*    (2006.01)
(Continued)

(52) U.S. Cl.
CPC ......... *A61B 5/4094* (2013.01); *A61B 5/0004* (2013.01); *A61B 5/0022* (2013.01);
(Continued)

(58) Field of Classification Search
CPC ... A61B 5/4094; A61B 5/1118; A61B 5/6804; A61B 5/0004; A61B 5/0402;
(Continued)

(56) References Cited

U.S. PATENT DOCUMENTS 3,815,611 A    6/1974   Denniston, III
4,197,856 A    4/1980   Northrop
(Continued)

FOREIGN PATENT DOCUMENTS

EP    1517298 A1    3/2005
EP    2123221 A2    11/2009
(Continued)

OTHER PUBLICATIONS

Extended European Search Report, dated Sep. 6, 2017 based on PCT Application No. US2014/068246 (10 pages).
(Continued)

*Primary Examiner* — Rex R Holmes
(74) *Attorney, Agent, or Firm* — Pizarro Allen PC

(57) ABSTRACT

A method and apparatus for monitoring a patient for seizure activity including collecting and processing EMG signal data and categorizing the detected data to execute risk stratification. A transmission protocol that is tailored for detected events may be selected and executed.

11 Claims, 11 Drawing Sheets

Related U.S. Application Data continuation-in-part of application No. 13/275,309, filed on Oct. 17, 2011, now Pat. No. 8,983,591.

(60) Provisional application No. 62/050,054, filed on Sep. 12, 2014, provisional application No. 62/032,147, filed on Aug. 1, 2014, provisional application No. 62/001,302, filed on May 21, 2014, provisional application No. 61/979,225, filed on Apr. 14, 2014, provisional application No. 61/969,660, filed on Mar. 24, 2014, provisional application No. 61/910,827, filed on Dec. 2, 2013, provisional application No. 61/504,582, filed on Jul. 5, 2011, provisional application No. 61/393,747, filed on Oct. 15, 2010.

(51) Int. Cl.

| | |
|---|---|
| *A61B 5/0488* | (2006.01) |
| *A61B 5/0402* | (2006.01) |
| *A61B 5/11* | (2006.01) |
| *G06F 19/00* | (2018.01) |
| *G16H 40/67* | (2018.01) |
| *A61B 5/01* | (2006.01) |

(52) U.S. Cl.
CPC ........ *A61B 5/0402* (2013.01); *A61B 5/04015* (2013.01); *A61B 5/0488* (2013.01); *A61B 5/1118* (2013.01); *A61B 5/6804* (2013.01); *A61B 5/7264* (2013.01); *A61B 5/7282* (2013.01); *A61B 5/746* (2013.01); *G06F 19/00* (2013.01); *G16H 40/67* (2018.01); *A61B 5/01* (2013.01); *A61B 2505/07* (2013.01)

(58) Field of Classification Search
CPC ... A61B 5/04015; A61B 5/746; A61B 5/0488; A61B 5/0022; A61B 5/7282; A61B 5/7264; A61B 2505/07; A61B 5/01
See application file for complete search history.

(56) References Cited

U.S. PATENT DOCUMENTS

| | | | |
|---|---|---|---|
| 4,566,464 A | 1/1986 | Piccone et al. | |
| 4,878,498 A | 11/1989 | Abrams et al. | |
| 5,263,489 A | 11/1993 | Johnson et al. | |
| 5,269,302 A | 12/1993 | Swartz et al. | |
| 5,301,680 A | 4/1994 | Rosenberg | |
| 5,311,876 A | 5/1994 | Olsen et al. | |
| 5,349,962 A | 9/1994 | Lockard et al. | |
| 5,373,852 A | 12/1994 | Harrison et al. | |
| 5,743,860 A | 4/1998 | Hively et al. | |
| 5,769,778 A | 6/1998 | Abrams et al. | |
| 5,810,747 A | 9/1998 | Brudny et al. | |
| 5,871,517 A | 2/1999 | Abrams et al. | |
| 5,879,309 A | 3/1999 | Johnson et al. | |
| 5,959,529 A | 9/1999 | Kail, IV | |
| 5,995,868 A | 11/1999 | Dorfmeister et al. | |
| 6,016,449 A | 1/2000 | Fischell et al. | |
| 6,018,682 A | 1/2000 | Rise | |
| 6,238,338 B1 | 5/2001 | Deluca et al. | |
| 6,315,740 B1 | 11/2001 | Singh | |
| 6,440,067 B1 | 8/2002 | DeLuca et al. | |
| 6,471,087 B1 | 10/2002 | Shusterman | |
| 6,473,639 B1 | 10/2002 | Fischell et al. | |
| 6,549,804 B1 | 4/2003 | Osorio et al. | |
| 6,597,944 B1 | 7/2003 | Hadas | |
| 6,643,541 B2 | 11/2003 | Mok et al. | |
| 6,678,549 B2 | 1/2004 | Cusimano et al. | |
| 6,819,956 B2 | 11/2004 | DiLorenzo | |
| 6,950,688 B2 | 9/2005 | Axelgaard et al. | |
| 7,024,247 B2 | 4/2006 | Gliner et al. | |
| 7,160,252 B2 | 1/2007 | Cho et al. | |
| 7,188,151 B2 | 3/2007 | Kumar et al. | |
| 7,209,787 B2 | 4/2007 | DiLorenzo | |
| 7,231,254 B2 | 6/2007 | DiLorenzo | |
| 7,242,984 B2 | 7/2007 | DiLorenzo | |
| 7,277,758 B2 | 10/2007 | DiLorenzo | |
| 7,539,533 B2 | 5/2009 | Tran | |
| 8,386,025 B2 | 2/2013 | Hoppe | |
| 8,983,591 B2 | 3/2015 | Leininger et al. | |
| 9,186,105 B2 | 11/2015 | Leininger et al. | |
| 2002/0177882 A1 | 11/2002 | DiLorenzo | |
| 2003/0109905 A1 | 6/2003 | Mok et al. | |
| 2003/0236474 A1 | 12/2003 | Singh | |
| 2004/0131998 A1 | 7/2004 | Marom et al. | |
| 2005/0081847 A1 | 4/2005 | Lee et al. | |
| 2005/0177400 A1 | 8/2005 | Rosenfeld et al. | |
| 2005/0277844 A1 | 12/2005 | Strother et al. | |
| 2006/0004299 A1 | 1/2006 | Endo et al. | |
| 2006/0025697 A1 | 2/2006 | Kurzwweil et al. | |
| 2007/0150024 A1 | 6/2007 | Leyde et al. | |
| 2007/0204691 A1 | 9/2007 | Bogner et al. | |
| 2007/0208212 A1 | 9/2007 | DiLorenzo | |
| 2007/0208263 A1 | 9/2007 | John et al. | |
| 2007/0287931 A1 | 12/2007 | DiLorenzo | |
| 2008/0001735 A1 | 1/2008 | Tran | |
| 2008/0005838 A1 | 1/2008 | Wang Fong et al. | |
| 2008/0077039 A1 | 3/2008 | Donnett et al. | |
| 2008/0082019 A1 | 4/2008 | Ludving et al. | |
| 2008/0091089 A1 | 4/2008 | Guillory et al. | |
| 2008/0091090 A1 | 4/2008 | Guillory et al. | |
| 2008/0146958 A1 | 6/2008 | Guillory et al. | |
| 2009/0054737 A1 | 2/2009 | Magar et al. | |
| 2009/0062696 A1 | 3/2009 | Nathan et al. | |
| 2009/0137921 A1 | 5/2009 | Kramer et al. | |
| 2010/0121213 A1 | 5/2010 | Giftakis et al. | |
| 2010/0121215 A1 | 5/2010 | Giftakis et al. | |
| 2010/0137735 A1 | 6/2010 | Hoppe | |
| 2010/0198098 A1 | 8/2010 | Osorio et al. | |
| 2012/0029322 A1 | 2/2012 | Wartena et al. | |
| 2012/0029390 A1 | 2/2012 | Colborn | |
| 2012/0083700 A1 | 4/2012 | Osorio | |
| 2012/0083701 A1 | 4/2012 | Osorio | |
| 2012/0108999 A1 | 5/2012 | Leininger et al. | |
| 2012/0116183 A1 | 5/2012 | Osorio | |
| 2012/0123232 A1 | 5/2012 | Najarian et al. | |
| 2012/0197092 A1 | 8/2012 | Luo et al. | |
| 2012/0226108 A1 | 9/2012 | Osorio | |
| 2012/0283526 A1 | 11/2012 | Gommesen et al. | |
| 2012/0310050 A1* | 12/2012 | Osorio ................. | A61B 5/4094 600/300 |
| 2013/0012830 A1 | 1/2013 | Leininger et al. | |
| 2013/0060167 A1 | 3/2013 | Dracup et al. | |
| 2013/0116514 A1 | 5/2013 | Kroner et al. | |
| 2013/0154827 A1 | 6/2013 | Housley | |
| 2013/0281797 A1 | 10/2013 | Sabesan | |
| 2014/0163413 A1 | 6/2014 | Conradsen et al. | |
| 2014/0275831 A1 | 9/2014 | Osorio | |
| 2014/0276181 A1 | 9/2014 | Sun et al. | |
| 2014/0276238 A1 | 9/2014 | Osorio | |

FOREIGN PATENT DOCUMENTS

| | | |
|---|---|---|
| JP | 2003220046 | 8/2013 |
| WO | WO9531932 | 3/1995 |
| WO | WO9726823 | 7/1997 |
| WO | WO02052293 | 1/2002 |
| WO | WO2004066832 | 8/2004 |
| WO | WO2006008334 | 1/2006 |
| WO | WO2006094513 | 9/2006 |
| WO | WO2006134359 | 12/2006 |
| WO | WO2007034476 | 3/2007 |
| WO | WO2007142523 | 12/2007 |
| WO | WO2008057365 | 5/2008 |
| WO | WO2008106054 | 9/2008 |
| WO | WO2008131782 | 11/2008 |
| WO | WO2009081206 | 7/2009 |
| WO | WO2011072684 | 6/2011 |
| WO | WO2012051628 | 4/2012 |
| WO | WO2012102974 | 8/2012 |

(56) References Cited

FOREIGN PATENT DOCUMENTS

| WO | WO2013006728 | 1/2013 |
|---|---|---|
| WO | WO2013185775 A1 | 12/2013 |

OTHER PUBLICATIONS

MR James et al, "Pulse oximetry during apparent tonic-clonic seizures" The Lancet, vol. 337, Feb. 16, 1991, pp. 394-395 (2 pages).
Che-Chang Yang and Yeh-Liang Hsu, "A review of accelerometry-based wearable motion detectors for physical activity monitoring" Medline, vol. 10, No. 8, Aug. 20, 2010 pp. 7772-7788 (17 pages).
Beniczky Sandor et al., "Detection of Generalized tonic-clonic seizures by a wireless wrist accelerometer: A prospective, multi-center center," Epilepsia, vol. 54, No. 4, Feb. 8, 2013 pp. e58-e61 (4 pages).
Conradsen, et al., "Evaluation of novel algorithm embedded in a wearable sEMG device for seizure detection," 34th Annual International Conference of the IEEE EMBS, San Diego, California, USA, Aug. 28-Sep. 1, 2012, pp. 2048-2051. (4 Pages).
Conradsen, et al., "Seizure Onset Detection based on a Uni- or Multi-modal Intelligent Seizure Acquisition (UISA/MISA) System," 32nd Annual International Conference of the IEEE EMBS Buenos Aires, Argentina, Aug. 31-Sep. 4, 2010, pp. 3269-3272. (4 Pages).
Conradsen, et al., "Dynamics of muscle activation during tonic-clonic seizures," Epilepsy Research, vol. 104, Issues 1-2, Mar. 2013, pp. 84-93 (10 Pages).
Sandor Beniczky, et al., "Quantitative analysis of surface electromyography during epileptic and nonepileptic convulsive seizures," Epilepsia, vol. 55, Issue 7, Jul. 2014, pp. 1128-1134. (7 Pages).
Rens Wientjes, "Potential Value of Surface Electromyography for Automated Epileptic Seizure Detection for Children in a Home Monitoring System," Eindhoven University of Technology Department of Electrical Engineering Signal Processing Systems, Master of Science Thesis, Project Period May 2006-Aug. 2007, Report 1107, pp. 1-101. (89 Pages).
Conradsen, et al., "Patterns of Muscle Activation During Generalized Tonic and Tonic-Clonic Epileptic Seizures," Wiley Periodicals, Inc., 2011 copyright International League Against Epilepsy, pp. 1-8. (8 Pages).
Conradsen, et al., "Multi-Modal Intelligent Seizure Acquisition (MISA) System—A New Approach Towards Seizure Detection Based on Full Body Motion Measures," 31st Annual International Conference of the IEEE EMBS Minneapolis, Minnesota, USA, Sep. 2-6, 2009, pp. 2591-2595. (5 Pages).
Uri Kramer, et al., "A Novel Portable Seizure Detection Alarm System: Preliminary Results," Journal of Clinical Neurophysiology, vol. 28, No. 1, Feb. 2011, pp. 36-38. (3 Pages).
Kris Cuppens, et al., "Detection of Nocturnal Frontal Lobe Seizures in Pediatric Patients by Means of Accelerometers: A First Study," 31st Annual International Conference of the IEEE EMBS, Minneapolis, Minnesota, USA, Sep. 2-6, 2009, pp. 6608-6611. (4 Pages).
Dutch Epilepsy Clinics Foundation Automates the Detection and Diagnosis of Epileptic Seizures with Simulink and the Video and Image Processing Blockset, www.mathworks.com, 91399v00 Jun. 2006, Page Accessed, Jun. 2006. (2 Pages).
Epilepsy Detector Application, http://www.epdetect.com/index. html, Page accessed, Sep. 2009. (6 Pages).
"Medpage ST-2; Movement Sensor Epileptic Seizure Monitor Alarm System with Breathing Monitor Alarm," http://wwww.medpage-ltd.com/page65.html, Page accessed Sep. 2009. (6 Pages).
"NeuroPace—Product," http://www.neuropace.com/product/overview.html, Page accessed Sep. 2009. (2 Pages).
NeuroVista, http://www.neurovista.com/research.html, Page accessed, Sep. 2009. (1 Page).
"Standards for Reporting Electromyography Data," Journal of Athletic Training, available at http://www.nata.org/jat/authors/electromyography_data.htm . First Published 1996 (4 Pages).
B. Bigland-Ritchie, et al., "Muscle Temperature, Contractile Speed, and Motoneuron Firing Rates During Human Voluntary Contractions," The American Physiological Society 0161-7567/92, 1992, pp. 2457-2461. (5 Pages).
B. Bigland-Ritchie, et al., "Conduction Velocity and EMG Power Spectrum Changes in Fatigue of Sustained Maximal Efforts," The American Physiological Society 0161/7567/81/0000-0000, 1981, pp. 1300-1305. (6 Pages).
Juliana Lockman, et al., "Detection of Seizure-Like Movements Using a Wrist Accelerometer," Epilepsy & Behavior 20 (2011) 638-641. (4 Pages).
Conradsen et al., "Automatic Multi-modal intelligent seizure acquistion (MISA) system for detection of motor seizures from electromyographic data and motion data," Computer Methods and Programs in Biomedicine 107 (2012) 97-110 (14 Pages).
Poh et al., "Convulsive Seizure Detection Using a Wrist-Worn Electrodermal Activity and Accelerometry Biosensor" Epilepsia, 53(5) e93-e97 (2012) (5 Pages).
Jean_Marc Le Caillec, Rene Garello "Comparison of Statistical Indices using Third Order Statistics for Nonlinearity Detection" in Signal Processing, vol. 84, Issue 3, Mar. 2004, pp. 499-525. (26 Pages).
Xue Wang, Yonghong Chen, "Testing for Statistical Significance in Bispectra: A Surrogate Data Approach and Application to Neuroscience" in IEEE Transactions on Biomedical Engineering, vol. 54, No. 11, Nov. 2007, pp. 1974-1982. (9 pages).
A. Dahaba et al. "Bispectral Index (BIS) monitoring of acute encephalitis with refractory, repetitive partial seizures (AERRPS)" in Minerva Anestesiologica, Apr. 2010 pp. 298-201. (4 pages).
K. Chua et al. "Application of higher order statistics/spectra in biomedical signals—A review" in Medical Engineering & Physics vol. 32 Issue 7, Sep. 2010 pp. 679-689. (11 pages).
N. Thakor and S. Tong "Advances in Quantitative Electroencephalogram Analysis Methods" in Annu. Rev. Biomed. Eng. vol. 6 Apr. 2004 pp. 453-495. (48 pages).
Muthuswamy et al. "Higher-Order Spectral Analysis of Burst Patterns in EEG" in IEEE Transactions in Biomedical Engineering, vol. 46, No. 1, Jan. 1999. (8 pages).
Karayiannis, N.B., et al. "Detection of pseudosinusoidal epileptic seizure segments in the neonatal EEG by cascading a rule-based algorithm with a neural network," Biomedical Engineering, IEEE Transactions, vol. 53, Issue 4, Apr. 2006, pp. 633-641. (9 Pages).
Optima Neuroscience, http://www.optimaneuro.com/products.php Page Accessible Apr. 2008. (1 Page).
Epilepsy Phenome/Genome Project, A Community Effort to Understand the Genetics of Epilepsy, http://www.epilepsy.com/group_discussion/975973 (Page Accessible 2008) (19 pages).
Abdulhamit Subasi, "Automatic Detection of Epileptic Seizure Using Dynamic Fuzzy Neural Networks," http://www.sciencedirect.com; Oct. 4, 2005 (6 pages).
File History of U.S. Pat. No. 5,349,962, Completed 1994, (250 pages).
International Search Report and Written Opinion in PCT/US2011/056601, dated Feb. 1, 2012 (12 Pages).
International Search Report and Written Opinion in PCT/US2012/045609, dated Jan. 25, 2013 (14 Pages).
International Search Report and Written Opinion in PCT/US2014/068246, dated Mar. 2, 2015 (14 Pages).

* cited by examiner

METHOD AND APPARATUS FOR CLASSIFICATION OF SEIZURE TYPE AND SEVERITY USING ELECTROMYOGRAPHY

CROSS REFERENCE TO RELATED APPLICATIONS

This application claims priority to International Application No. PCT/US2014/068246 filed Dec. 2, 2014, U.S. Provisional Patent Application No. 62/001,302 filed May 21, 2014, U.S. Provisional Patent Application No. 62/050,054 filed Sep. 12, 2014, U.S. Provisional Patent Application No. 62/032,147 filed Aug. 1, 2014, U.S. Provisional Patent Application No. 61/979,225 filed Apr. 14, 2014, U.S. Provisional Patent Application No. 61/969,660 filed Mar. 24, 2014, U.S. Provisional Patent Application No. 61/910,827 filed Dec. 2, 2013, and is a continuation-in-part of U.S. patent application Ser. No. 13/275,309 filed Oct. 17, 2011, which issued as U.S. Pat. No. 8,983,591 on Mar. 17, 2015, which claims priority to U.S. Provisional Patent Application Ser. No. 61/393,747 filed Oct. 15, 2010, and a continuation-in-part of U.S. patent application Ser. No. 13/542,596 filed Jul. 7, 2012, which issued as U.S. Pat. No. 9,186,105 on Nov. 17, 2015, which claims priority to U.S. Provisional Patent Application Ser. No. 61/504,582 filed Jul. 5, 2011. The disclosure of all of the above are herein fully incorporated by reference.

BACKGROUND

A seizure may be characterized as abnormal or excessive synchronous activity in the brain. At the beginning of a seizure, neurons in the brain may begin to fire at a particular location. As the seizure progresses, this firing of neurons may spread across the brain, and in some cases, many areas of the brain may become engulfed in this activity. Seizure activity in the brain may cause the brain to send electrical signals through the peripheral nervous system to different muscles the activation of which may initiate a redistribution of ions within muscle fibers. In electromyography (EMG), an electrode may be placed on or near the skin and configured to measure changes in electrical potential resulting from ion flow during this muscle activation.

Techniques designed for studying and monitoring seizures have typically relied upon electroencephalography (EEG), which characterizes electrical signals using electrodes attached to the scalp or head region of a seizure prone individual or seizure patient. Detecting an epileptic seizure using electroencephalography (EEG) typically requires attaching many electrodes and associated wires to the head and using amplifiers to monitor brainwave activity. The multiple EEG electrodes may be very cumbersome and generally require some technical expertise to apply and monitor. Confirmation of a seizure typically requires observation in an environment provided with video monitors and video recording equipment. Furthermore, when measuring brain activity with EEG, not all measured activity of or relating to a seizure may actually be manifested as an event that is likely to be dangerous. And, EEG data without video corroboration may not be suited to grade or differentiate some seizures, including those that may be weak or only of minimal concern, from other seizures that may be more dangerous.

Unless used in a staffed clinical environment, EEG equipment is frequently not intended to determine if a seizure is in progress but rather provide a historical record of the seizure after the incident. And, that equipment is usually designed for hospital-like environments where a video camera recording or caregiver's observation may provide corroboration of the seizure, and is typically used as part of a more intensive care regimen such as a hospital stay for patients who experience multiple seizures. A hospital stay may be required for diagnostic purposes or to stabilize a patient until suitable medication can be administered. Upon discharge from the hospital, a patient may be sent home with little further monitoring. However, at any time after being sent home the person may experience another seizure, perhaps fatal.

A patient should in some cases be monitored at home for some length of time in case another seizure should occur. Seizures with motor manifestations may have patterns of muscle activity that include rhythmic contractions of some, most, or all of the muscles of the body. A seizure could, for example, result in Sudden Unexplained Death in Epilepsy (SUDEP). The underlying causes of SUDEP are not well understood; however, in some cases, severe central nervous system depression may follow a seizure. Following central nervous system depression, breathings rates may increase and decrease in a cycle that may result in cardiac dysrhythmia and death. However, not all seizures have the same likelihood of causing or being associated with SUDEP, and in some patients, some seizure activity may be present without significant risk of SUDEP. And, without differentiation of seizures by type, severity or further classification, it may be difficult to selectively identify seizure activity that is most likely to be dangerous.

While there presently exist ambulatory devices for diagnosis of seizures, they are EEG-based and are generally not designed or suitable for long-term home use or daily wearability. Other seizure alerting systems may operate by detecting motion of the body, usually the extremities. Such systems may generally operate on the assumption that while suffering a seizure, a person will move erratically and violently. However, depending upon the type of seizure, this assumption may or may not be true. Electrical signals sent from the brain during the seizure are frequently transmitted to many muscles simultaneously, which may result in muscles fighting each other and effectively canceling out violent movement. In other words, the muscles may work to make the person rigid rather than cause actual violent movement. Thus, the seizure may not be consistently detected with accelerometer-based detectors.

Accordingly, there is a need for an epileptic seizure detection method and apparatus that can be used in a non-institutional or institutional environment without many of the cumbersome electrodes to the head or extremities and that accurately detects seizure events with motor manifestations but that is not limited to responding to violent motions. There is still further, a need for epileptic seizure detection methods that differentiate for caregivers weak motor manifestation that may not demand an emergency response from other types of seizures including those may demand emergency intervention.

SUMMARY

A method of monitoring a patient for seizure activity including collecting EMG signal data; processing the collected EMG signal data to determine if a detected event is present; categorizing the detected event including risk stratification and selecting, based, for example, on the categorization and risk assessment, a transmission protocol included among a group of selectable transmission protocols. Upon selection of a transmission protocol an appropriate transmission, such as an alarm or warning message, may be sent to caregivers and/or to designated individuals.

DETAILED DESCRIPTION

Figure 1:
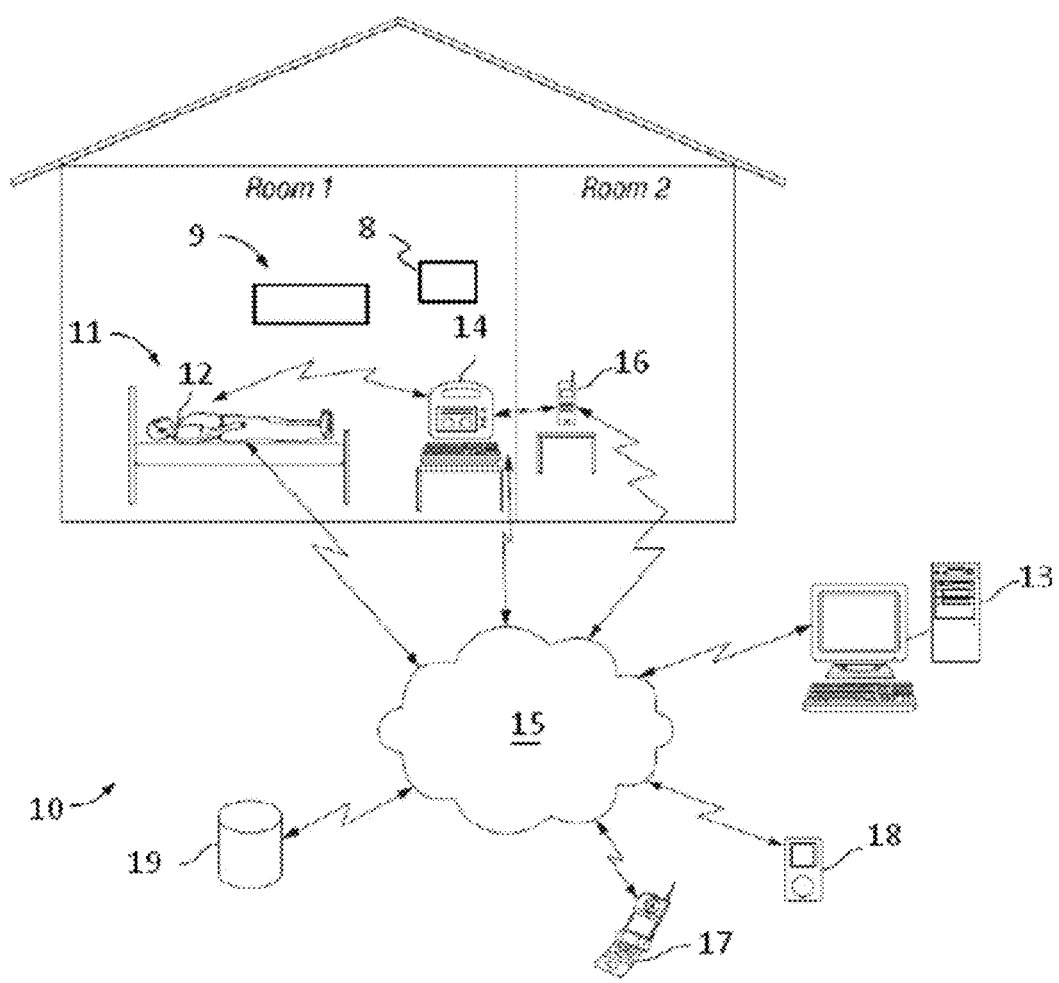
FIG. 1 illustrates one embodiment of a seizure detection system.

The apparatuses and methods described herein may be used to detect seizures and timely alert caregivers of seizure-related events. The apparatuses may include sensors attached to a patient or patient's clothing and may be configured for measurement of muscle electrical activity using electromyography (EMG). Detection of seizures using EMG electrodes is further described, for example, in Applicant's U.S. patent application Ser. Nos. 13/275,309 and 13/542,596 and Applicant's U.S. Provisional Patent Application Nos. 61/875,429, 61/894,793, 61/969,660, and 61/979,225 the disclosures of each of which are herein fully incorporated by reference. As described herein, apparatuses and methods may be used to monitor a patient for muscle electrical activity using EMG, detect possible seizure events, and stratify detected events based on risk, type, and/or severity. If a detected event, including, for example, a seizure of a given type or severity is deemed present, the monitoring system may then select a certain transmission protocol for warning of one or more caregivers. A transmission protocol may, for example, include sending either of an alarm message and/or EMG signal data over a network to one or more caregivers or other designated individuals.

In some embodiments, transmitted EMG data may be organized to encourage verification or review of detected events. A caregiver may, for example, in response to detection of some events, be sent information to easily scan and review time and/or frequency domain EMG data. In addition to raw signal data, other information associated with analyzed EMG signal data may also be transmitted. For example, in some embodiments, one or more patterns typical of abnormal muscle movements may be identified from among noisy data, and the particular patterns identified may be communicated to the caregiver. Other statistical data related to detected events, including, for example, statistical data associated with detection of qualified peak data may also be transmitted to a caregiver. In some embodiments, that information may be sent and/or presented to a user based on system or user defined preferences.

In some embodiments, risk stratification may facilitate transmission of either or both of an alarm message and/or more data rich information, such as time and/or frequency domain EMG data. Moreover, stratification may facilitate selection of transmission protocols that minimize power consumption. And, in some embodiments, some detected events may be deemed suitable to be safely ignored or communicated to a remote user as only demanding a warning alarm status. For example, it may be deemed that a detected event may pose only minimal risk of SUDEP, injury from falling, and/or pose only minimal risk from other concerns. A caregiver may then, for example, be given a message that the event was detected but that an emergency response is not warranted and/or the event may be logged in a searchable database for post-hoc review.

Data transmitted from a monitoring system, may, in some embodiments, be customized for a particular individual or recipient group. For example, transmitted data may include, an alarm message, subset of statistical information related to algorithm detection, time or frequency domain EMG data, other data, and/or combinations thereof. And, that information may be useful to a certain subset of data recipients, but it may not be useful (or it may be detrimental) to send that information to other recipients. For example, an emergency medical technician (EMT) may be sent alarm information related to a patient including some sensor data, but the EMT may not be suitably trained to interpret all EMG data. And, sending that data may be a burden and/or confuse the caregiver during an emergency response. However, other caregivers, such as the doctor of a patient with epilepsy or remote individuals trained to more fully interpret EMG signal data, may be sent a more extensive portion of available data including, for example, information suitable to reconstruct the time dependence of the collected EMG signal or information suitable to evaluate the output of algorithms used for identification of one or more patterns of muscle activity.

Data sent from a monitoring system may be related to the status of a detected event, including, for example, whether the detected event was classified as an emergency or warning event. Data may further be organized for transmission to any of a group of selected or designated individuals, including, in addition to caregivers, any number of other individuals such as, for example, chosen friends and family.

In some embodiments, a monitoring system may send data to a remote database or server. Designated individuals may have access to the data included therein or to a certain or restricted portion of data that is stored therein. To view data an individual may, in some embodiments, log on to a remote database and information may be sent from that database to the individual. Therefore, data may, in some embodiments, be presented to an individual directly from a patient device (e.g., detection unit or base station), from a remote database, or from both sources.

In some embodiments, methods herein may detect and classify weak seizures or other events that may be identified, but may not warrant an emergency response. That classification, may, for example, depend on detection of seizure characteristics selectively present in either of the tonic and/or clonic phases of a seizure. Furthermore, classification may, in some embodiments, include an analysis of the temporal relationship between seizure phases and/or attributes of detected EMG signal collected in intermediate periods between detected phases. For example, classification may, in some embodiments, include determining whether each of a tonic and clonic phase of a seizure are detected and whether those phases are present consecutively, such as with or without a period of decreased activity between them. And, in some embodiments, as further described herein, risk stratification may further include additional sensor and/or other data. For example, in some embodiments, risk stratification may include analysis of additional data such as may be added from one or more orientation, position, oxygen saturation, or pulse oximeter sensors.

Systems described herein may be suitable for monitoring of a patient in an ambulatory setting, and may include one or more EMG sensors that may be coupled to skin on or near one or more muscles of a patient. EMG signals may be collected in a substantially continuous manner, but it may be desirable to only send or alert a caregiver of a subset of the collected EMG signals. For example, particularly for mobile detection devices, power consumption for sending signal data may be significant, and it may, therefore, be desirable to limit an amount of the collected signal transmitted through a network. To accomplish that objective, risk stratification of detected events may, as described herein, be used—a functionality that is notably absent from other monitoring systems.

In some embodiments, thresholds suitable for detection of weak seizure events may be set. And, those settings may be used without burdening a monitoring system with risk of an inordinate number of false positive detections. For example, thresholds suited for identification of weak seizure-related events may be set to identify those events, but because detected events may be automatically classified and appropriate transmission protocols selected only a subset of detection events may automatically initiate an emergency response. Therefore, the system may still warn a caregiver of the presence of those events and/or link those events to a searchable database, but inappropriate emergency response or false-positive-detections may be limited.

EMG may be ideally suited for this purpose for a number of reasons. For example, while a great deal of information may be available from EEG collected data, electrical signals in the brain do not always correlate reliably with a true seizure or with a seizure of a given type or risk. And, looking at muscle motor manifestations of brain activity may provide a more accurate route to classification of seizures by severity and type. And, using EMG, as described herein, different parts of seizure activity may be selectively identified. For example, signal elevations in EMG may be transient or sustained, and for example, by selecting certain detection settings based on the width of detected signals or other factors, as also described, for example, in Applicant's Provisional Application No. 61/969,660, one may configure a detection routine to be selective for a particular part of seizure activity. Importantly, because different types of seizures may be detected, seizure data may be risk stratified based on whether parts most likely to demand a certain response are detected.

An executed response to a detected event may be tailored based upon characteristics of the detected event. For example, understanding whether a sensor signal may be related to a Tonic-Clonic, Tonic-only, Clonic-only, or other type of seizure may enable caregivers to better evaluate detected events and plan an appropriate response. Furthermore, some seizures may be brief and/or lack characteristic signatures of more intense seizures, such as repetitive motions that may occur in clonic-phase portions of a seizure. At least some of those seizures may be detected as an increase in magnitude of EMG signal or detected using other more sophisticated algorithms or devices, but while such seizures may be detected and may trigger an alarm, they may, for some patients, present only limited or insignificant risk of injury. For example, some detected events may generally not pose a significant risk of adverse effects of having a seizure including SUDEP. If such detections are made without further classification, unnecessary, and cost-prohibitive signaling of alarms in response to non-threatening events may be the only way to also respond to potentially dangerous events. Methods herein may alleviate such concerns by processing data to facilitate a tailored and more cost-effective strategy for patient monitoring such as by estimating whether individual detected events pose a significant risk of adverse effects of a seizure.

In some embodiments, methods herein may classify a detected seizure based on seizure profiles for the patient or for a patient demographic. For example, a detected seizure may be classified based on various metrics, including, by way of nonlimiting example, type, intensity, seizure duration, duration of a seizure phase, other metrics, and combinations thereof. Classification of the severity of a seizure may, for example, include normalizing metrics of the seizure against values typical of a patient or patient demographic. For example, for a patient, if a measured magnitude of a detected characteristic is some factor of a previously measured value for the characteristic (e.g., during another seizure for the patient) or some factor of an average value for the characteristic that factor may be used to grade the seizures severity. For example, a certain seizure may be detected, and the characteristic detected may only have a magnitude that is only 50% (or some other factor) as great as in other seizures detected for the patient. That information may, for example, be sent to caregivers and/or otherwise used to determine an appropriate response. For example, it may be known that the patient may typically have a number of weak seizures and that for that patient risk of adverse effects of those seizures may be low. And, at least some detected events may be safely ignored or ignored in some situations. For example, if the patient experiences only a weak seizure and if the patient is known to be in bed resting then risk of both SUDEP and risk of falling may be low. And, in some embodiments, at least some detected events may be ignored or may only be logged as an event that may not need an emergency response.

Along with or in addition to alarm initiation, apparatuses and method described herein may also be used to create a log of seizure events to help medically or surgically manage a patient. To facilitate organization of detected seizure or possible seizure-related events, events may be classified. For example, automatic classification of seizure events (e.g., based on type and/or severity) may be used in the creation of ordered databases of seizure-related data particularly where video corroboration of events is absent or where individual review of sizeable sets of data by trained professionals, such as medical doctors, would be inconvenient or prohibitively costly.

In some embodiments, methods herein may include identification of regions of EMG signal including processed signal with elevated amplitude and further identify regions that are peaks (e.g., regions where signal amplitude, including processed signal amplitude, rises and falls). Peaks that rise and fall, and which include regions of elevated signal amplitude present for limited time periods of time may be identified. Identified peaks may, as further described herein, be qualified against one or more properties typically present in the clonic-phase of a seizure, and may be qualified to increase selectivity for detection of the clonic-phase of a seizure. For example, a peak may be compared against one or more properties of EMG signal data from one or more patients experiencing a clonic-phase of a seizure or compared against changes that occur during physiological transformation into a clonic-phase and qualified to be similar to the aforementioned clonic-phase properties and/or changes. In this disclosure, such a qualified peak may be referred to as a "clonic-phase burst." The presence of a critical level of clonic-phase burst activity may, for example, be used to detect the presence of clonic-phase activity of a seizure.

In some embodiments, methods herein may include identification of regions of EMG signal including processed signal with elevated amplitude and further identify an initial group that are peaks (e.g., regions where signal amplitude, including processed signal amplitude, rises and falls). That set of identified peaks may then be subject to qualification as may be used to determine the presence of clonic-phase bursts. Amplitude may refer to either the magnitude of signal, or absolute value of magnitude, as may be appropriate for a given calculation and/or signal form. Signals collected may, for example, be rectified, and EMG signal amplitude may refer to the magnitude of rectified signal from an EMG sensor. In some embodiments, an EMG signal may be processed to isolate one or more frequency bands and the amplitude of a signal may refer to a magnitude of signal isolated for the one or more frequency band or to a magnitude of a statistical value related to levels of motor activity and processed from isolated signal in the one more frequency bands. For example, in some embodiments, a statistical value may be a T-squared statistical value that is related to levels of motor activity.

Procedures for determining a group of peaks are described herein, but are also described, for example, in Applicant's U.S. patent application Ser. No. 13/275,309, which claims priority to Provisional Patent Application No. 61/875,429. In brief, in some embodiments, a peak-detection program may be executed to identify parts of EMG signal data that include one or more peaks. Identification of peaks may, for example, including detection of trailing and/or leading edges of peaks a procedure that may include searching for portions of EMG data or portions of smoothed EMG data where curvature of the data changes. For example, inflection or other critical points in a set of data may be identified and used to identify the presence of one or more peaks.

Qualification may then include identification or selection of peaks that meet one or more criterion. For example, peaks may be selected that meet criterion that increase confidence that the peaks are properly ascribed to patterns indicative clonic-phase activity. For example, peaks may be qualified to be clonic-phase bursts. At a high level, procedures for qualification of peak data as including one or more clonic-phase bursts may include comparison of various peak properties to one or more qualification thresholds. For example, if, for a peak, one or more peak property values related to clonic-phase activity meets one or more qualification thresholds a qualification criterion may be deemed satisfied and the peak may then be referred to as a clonic-phase burst.

Some qualification procedures may operate on individual peaks. That is, certain properties of a peak such as its height, area, or duration width may be defined without including data from other peaks. Therefore, individual values for the property may be calculated for each peak in a group. Other properties, as described below, may be calculated for more than one peak. Properties of individual peaks may include, for example, peak height, peak area, signal-to-noise ratio (SNR) (e.g., a ratio of peak amplitude to estimates of uncertainty in peak amplitude as may be measured or estimated from background regions), duration width, duration of intervening periods of lesser signal on either side of a peak, other properties of individual peaks and combinations thereof.

In some embodiments of methods herein, each identified peak in an initial group of peaks (e.g., a set prior to qualification) may be compared against qualification thresholds selected from the group of qualification thresholds including a minimum duration width, maximum duration width, minimum signal-to-noise ratio (SNR), minimum duration of one or more quiet or intervening periods on either said of a peak, maximum duration of one or more intervening periods on either said of a peak and/or combinations thereof. An intervening period may be defined by the duration length of a region of signal stability or low amplitude (e.g., low signal variability, RMS noise or signal magnitude) which may, for example, be marked by the distance between a peak edge and a nearby region of signal increase in magnitude or decrease in signal stability. In some embodiments, a signal-to-noise ratio for a peak may be calculated using amplitude data for the peak and an estimate or calculation of signal noise. Noise may, for example, be determined by calculating or estimating a level of variation or uncertainty in a baseline signal (e.g., uncertainty in measurement of signal amplitude, height, or area that may result from fluctuations in EMG data for a region not associated with peak activity of interest) which may, for example, be determined from data collected on either side of a peak or from a separately measured portion of an EMG signal such as a portion where a patient is at rest. To calculate noise, for example, signal may be collected and signal variability may be directly measured. Alternatively, noise may, for example, be estimated from a signal magnitude and an estimate of variability expected from variations typical of a signal of that magnitude as predicted by one or more model functions, including for example, a normal distribution model function. In some embodiments, an estimate of variations or uncertainty in a baseline signal or noise may be selected or calculated during one or more system calibration routines.

In some embodiments of peak qualification, a peak may be qualified as clonic-phase burst by meeting a threshold SNR, by meeting a minimum threshold for peak duration width of about 25 to about 75 milliseconds, and by meeting a maximum threshold for peak duration width of about 250 milliseconds to about 500 milliseconds activity. In some embodiments, for a peak to qualify as a clonic-phase burst an intervening sequence of substantially quiet signal of about 50 milliseconds to about 300 milliseconds may be detected.

Some properties of peak data may be calculated for more than one peak. And, in some embodiments herein, procedures for qualification of clonic-phase bursts may include comparison of a plurality of peaks to one or more qualification thresholds. That is, a plurality of peaks may be selected, an aggregate property value for the plurality of peaks determined, and the aggregate property value compared to one or more associated thresholds.

A qualification threshold value related to a property of a group of peaks may be referred to as an aggregate qualification threshold value. For example, included among aggregate qualification threshold values that may be used to qualify a plurality of peaks are minimum and/or maximum rates of peak repetition and/or thresholds for variations in duration of times between peaks.

In some embodiments, a plurality of peaks may be qualified against a threshold value for minimum repetition rate of peaks of about one peak per second and a threshold value for maximum repetition rate of peaks of about seven peaks per second. In some embodiments, for example, if a greater number or lesser number of peaks than bounded by the above thresholds is present over an appropriate interval (e.g., an appropriate interval to scale a number of peaks as a peak rate), it may be deemed that the peaks may not be properly qualified.

Included among various metrics for characterizing variation in duration of times between peaks is an average deviation percentage as also described in Applicant's related application U.S. Ser. No. 13/275,309. However, other metrics for characterizing variability of peak timing such as standard deviation, average deviation or percentage deviation values are also described therein. Any of the aforementioned metrics of a plurality of peaks may be calculated and may be used as aggregate property values comparable to aggregate property threshold values as described herein. In some embodiments, a plurality of peaks may be qualified if a minimum average deviation percentage value for time between peaks is greater than about 1% or about 5%. That is, an aggregate property threshold value of minimum average deviation percentage may, in some embodiments, be between about 1% to about 5%. In some embodiments, a plurality of peaks may be qualified as a plurality of clonic-phase bursts if a maximum average deviation percentage value for time between peaks is less than about 40% or about 50%. Routines for determining variations duration of times between peaks are further explained in greater detail in various others of Applicant's copending applications incorporated herein by reference.

In some embodiments, a procedure for peak qualification may include an initial qualification step based on one or more criterion as described above (e.g., criterion based on individual peaks), removal of peaks that fail that initial qualification, and another qualification step based on calculation of one or more aggregate property values for remaining peaks (e.g., all peaks that meet the initial qualification). For example, peaks may be identified, some peaks removed from overall qualification (e.g., peaks may be removed because the peaks are too narrow or too wide), and then remaining peaks qualified if the remaining peak data as a whole meets one or more aggregate threshold criterion.

A variety of systems may be suitable for collecting large amounts of EMG and other patient-related data, organizing such data for system optimization, and for initiating an alarm in response to a suspected seizure. FIG. 1 illustrates an exemplary embodiment of such a system. In the embodiment of FIG. 1, a seizure detection system 10 may include a detection unit 12. The detection unit may be configured as a portable and wearable device disposed on or near (or even attached to) any suitable muscle or muscle groups that may be subject to motor manifestations during a seizure. And, in some embodiments, the system 10 may include any of various wireless local area network technologies. For example, a detection unit 12 may communicate wirelessly to the internet using WiFi, Bluetooth, or through another local network. And, using a local network a detection unit 12 may, in some embodiments, send data over the internet directly or via an intermediate base station 14. In some embodiments, a caregiver may be contacted directly through a local network such as WiFi. A base station 14 may be connected to the internet wirelessly (such as through a local network), or may be linked to the internet through a hard connection. And, in some embodiments, in addition to a detection unit 12 or in addition to a detection unit 12 and base station 14, a system 10 may, for example, include any of an acoustic sensor 8, a video camera 9, alert transceiver 16, or combination of the aforementioned elements. The detection unit may comprise one or more EMG electrodes capable of detecting electrical signals from muscles at or near the skin surface of a patient, and delivering those electrical EMG signals to a processor for processing. The EMG electrodes may be coupled or attached to a patient, and may, in some embodiments, be implanted within the tissue of a patient near a muscle that may be activated during a seizure. Implanted devices may, for example, be particularly amenable for some patients where EMG signals may typically be weak such as patients with significant adipose tissue. The base station may comprise a computer capable of receiving and processing EMG signals from the detection unit, acoustic data from an acoustic sensor, and/or data from other sensors, and determining from the processed signals whether a seizure may have occurred, and sending an alert to a caregiver. An alert transceiver 16 may be carried by, or placed near, a caregiver to receive and relay alerts transmitted by the base station or to the internet. Other components that may be included in the system 10, including for example, wireless device 17, 18, storage database 19, electronic devices for detecting changes in the integrity of an electrode skin interface, and one or more environmental transceivers are also described in Applicant's U.S. patent application Ser. Nos. 13/275,309 and 13/542,596 and Applicant's Provisional Application Nos. 61/894,793 and 61/875,429.

In using the apparatus of FIG. 1, for example, a person 11 susceptible to epileptic seizures may be resting in bed, or may be at some other location as daily living may include, and may have a detection unit 12 in physical contact with or in proximity to his or her body. The detection unit 12 may be a wireless device so that a person may be able to get up and walk around without having to be tethered to an immobile power source or to a bulkier base station 14. For example, the detection unit 12 may be woven into a shirt sleeve, may be mounted to an armband or bracelet, or may be an implanted device. In other embodiments, one or more detection units 12 or other sensors may be placed or built into a bed, a chair, an infant car seat, or other suitable clothing, furniture, equipment and accessories used by those susceptible to seizures. The detection unit 12 may comprise a simple sensor, such as an electrode, that may send signals to the base station for processing and analysis, or may comprise a "smart" sensor having some data processing and storage capability. A detection unit 12 may include one or more smart client applications. In some embodiments, a simple sensor may be connected via wire or wirelessly to a battery-operated transceiver mounted on a belt worn by the person.

The system may monitor the patient, for example, while resting, such as during the evening and nighttime hours. If the detection unit 12 on the patient detects a seizure, the detection unit 12 may communicate via wire or wirelessly, e.g., via a communications network or wireless link, with the base station 14, to a remote cell phone or other hand held or desktop device via bluetooth or simultaneously to a base station and remote cell phone or other device. A detection unit 12 may send some signals to the base station device for more thorough analysis. For example, the detection unit 12 may process and use EMG signals (and optionally, or in some embodiments, ECG, temperature, orientation sensors, saturated oxygen, and/or audio sensor signals) to make an initial assessment regarding the likelihood of occurrence of a seizure, and may send those signals and its assessment to the base station 14 for separate processing and confirmation. If the base station 14 confirms that a seizure is likely occurring, then the base station 14 may initiate an alarm for transmission over the network 15 to alert a designated individual by way of email, text, or any suitable wired or wireless messaging indicator. It should be appreciated that the detection unit 12 may, in some embodiments, be smaller and more compact than the base station and it may be convenient to use a power supply with only limited strength. Therefore, it may be advantageous, in some embodiments, to control the amount of data that is transferred between the detection unit 12 and the base station 14 as this may increase the lifetime of any power supply elements integrated in the detection unit 12. In some embodiments, if one or more of the detection unit 12, the base station 14, or a caregiver, e.g., a remotely located caregiver monitoring signals provided from the base station, determines that a seizure may be occurring a video monitor 9 may be triggered to collect information.

The base station 14, which may be powered by a typical household power supply and contain a battery for backup, may have more processing, transmission and analysis power available for its operation than the detection unit 12, may be able to store a greater quantity of signal history, and evaluate a received signal against that greater amount of data. The base station 14 may communicate with an alert transceiver 16 located remotely from the base station 14, such as in the bedroom of a family member, or to a wireless device 17, 18 carried by a caregiver or located at a work office or clinic. The base station 14 and/or transceiver 16 may send alerts or messages to designated people via any suitable means, such as through a network 15 to a cell phone 17, PDA 18 or other client device. The system 10 may thus provide an accurate log of seizures, which may allow a patient's physician to understand more quickly the success or failure of a treatment regimen. Of course, the base station 14 may simply comprise a computer having installed a program capable of receiving, processing and analyzing signals as described herein, and capable of transmitting an alert. A base station 14 may include one or more smart client applications. In other embodiments, the system 10 may simply comprise, for example, EMG electrodes as part of a device configured to transmit signal data to a smartphone, such as an iPhone, configured to receive EMG signals from the electrodes for processing the EMG signals as described herein using an installed program application. In further embodiments, so-called "cloud" computing and storage may be used via network 15 for storing and processing the EMG signals and related data. In yet other embodiments, one or more EMG electrodes could be packaged together as a single unit with a processor capable of processing EMG signals as disclosed herein and sending an alert over a network. In other words, the apparatus may comprise a single item of manufacture that may be placed on a patient and that does not require a base station separate transceiver. Or the base station may be a smartphone or tablet.

In the embodiment of FIG. 1, the signal data may be sent to a remote database 19 for storage. In some embodiments, signal data may be sent from a plurality of patients with epilepsy to a central database 19 and "anonymized" to provide a basis for establishing and refining generalized "baseline" sensitivity levels and signal characteristics of an epileptic seizure. The database 19 and base station 14 may be remotely accessed via network 15 by one or more remote computers 13 to allow updating of detector unit and/or base station software, and data transmission. And, in some embodiments, the remote computer 13 or another computer may also serve to monitor exchange of data including alarm signals and EMG signal data between different devices associated with any number of designated individuals set to receive the signal. The base station 14 may generate an audible alarm, as may a remote transceiver 16 or detection unit 12. All wireless links may be two-way for software and data transmission and message delivery confirmation. The base station 14 may also employ one or all of the messaging methods listed above for seizure notification. The base station 14 or detection unit 12 may provide an "alert cancel" button to terminate the incident warning.

In some embodiments, a transceiver may additionally be mounted within a unit of furniture or some other structure, e.g., an environmental unit or object. If a detection unit is sufficiently close to that transceiver, such a transceiver may be capable of sending data to a base station. Thus, the base station may be aware that information is being received from that transducer, and therefore the associated environmental unit. In some embodiments, a base station may select a specific template file, e.g., such as including threshold values and other data as described further herein, that is dependent upon whether or not it is receiving a signal from a certain transceiver. Thus, for example, if the base station receives information from a detector and from a transducer that is associated with a bed or crib it may treat the data differently than if the data is received from a transducer associated with another environmental unit, such as, for example, clothing typically worn while an individual may be exercising or an item close to a users sink where for example a patient may brush their teeth. More generally, a monitoring system may, in some embodiments, be configured with one or more elements with global positioning (GPS) capability, and position information may be used to adjust one or more routines that may be used in a detection algorithm. For example, GPS capability may be included along with or among one or more microelectromechanical sensor elements included in a detection unit.

The embodiment of FIG. 1 may be configured to be minimally intrusive to use while sleeping or minimally interfere in daily activities, may require a minimum of electrodes such as one or two, may require no electrodes to the head, may detect a seizure with motor manifestations, may alert one or more local and/or remote sites of the presence of a seizure, and may be inexpensive enough for home use.

Figure 2:
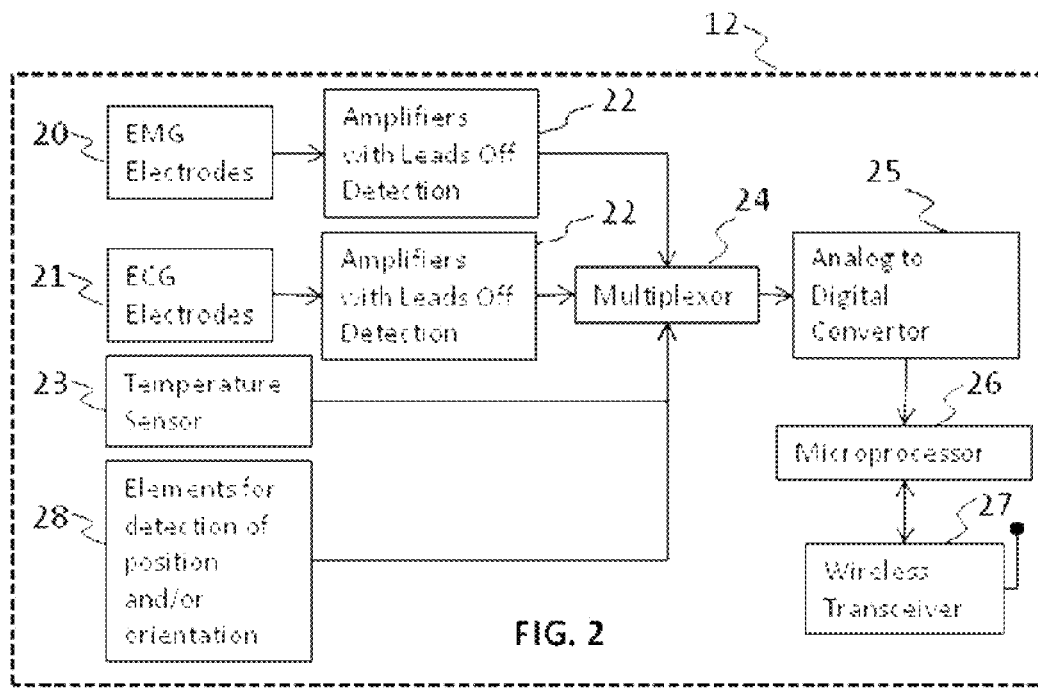
FIG. 2 illustrates one embodiment of a detection unit for a seizure detection system.

FIG. 2 illustrates an embodiment of a detection unit 12 or detector. The detection unit 12 may include EMG electrodes 20, and may also include, in some embodiments, ECG electrodes 21. The detection unit 12 may further include amplifiers with leads-off detectors 22. In some embodiments, one or more leads-off detectors may provide signals that indicate whether the electrodes are in physical contact with the person's body, or otherwise too far from the person's body to detect muscle activity, temperature, brain activity or other patient phenomena. The detection unit may further include one or elements 28, such as solid state microelectromechanical (MEMS) structures, configured for detection of position and/or orientation of the detection unit. For example, an element 28 may include one or more micromachined inertial sensors such as may include one or more gyroscopes, accelerometers, magnetometers or combinations thereof.

The detection unit 12 may further include a temperature sensor 23 to sense the person's temperature and one or more orientation or position sensitive elements 28. Other sensors (not shown) may be included in the detection unit, as well, such as accelerometers, microphones, and oximeters. Signals from electrodes 20 and 21, temperature sensor 23, orientation and/or position sensors 28 and other sensors may be provided to a multiplexor 24. The multiplexor 24 may be part of the detection unit 12 or may be part of the base station 14 if the detection unit 12 is not a smart sensor. The signals may then be communicated from the multiplexor 24 to one or more analog-to-digital converters 25. The analog-to-digital converters may be part of the detection unit 12 or may be part of the base station 14. The signals may then be communicated to one or more microprocessors 26 for processing and analysis as disclosed herein. The microprocessors 26 may be part of the detection unit 12 or may be part of the base station 14. The detection unit 12 and/or base station 14 may further include memory of suitable capacity. The microprocessor 26 may communicate signal data and other information using a transceiver 27. Communication by and among the components of the detection unit 12 and/or base station 14 may be via wired or wireless communication.

Of course, the exemplary detection unit of FIG. 2 may be differently configured. Many of the components of the detector of FIG. 2 may be in base station 14 rather than in the detection unit 12. For example, the detection unit may simply comprise an EMG electrode 20 in wireless communication with a base station 14. In such an embodiment. A-D conversion and signal processing may occur at the base station 14. If an ECG electrode 21 is included, then multiplexing may also occur at the base station 14.

In another example, the detection unit 12 of FIG. 2 may comprise an electrode portion having one or more of the EMG electrode 20, ECG electrode 21 and temperature sensor 23, in wired or wireless communication with a small belt-worn transceiver portion. The transceiver portion may include a multiplexor 24, an A-D converter 25, microprocessor 26, transceiver 27 and other components, such as memory and I/O devices (e.g., alarm cancel buttons and visual display).

Figure 3:
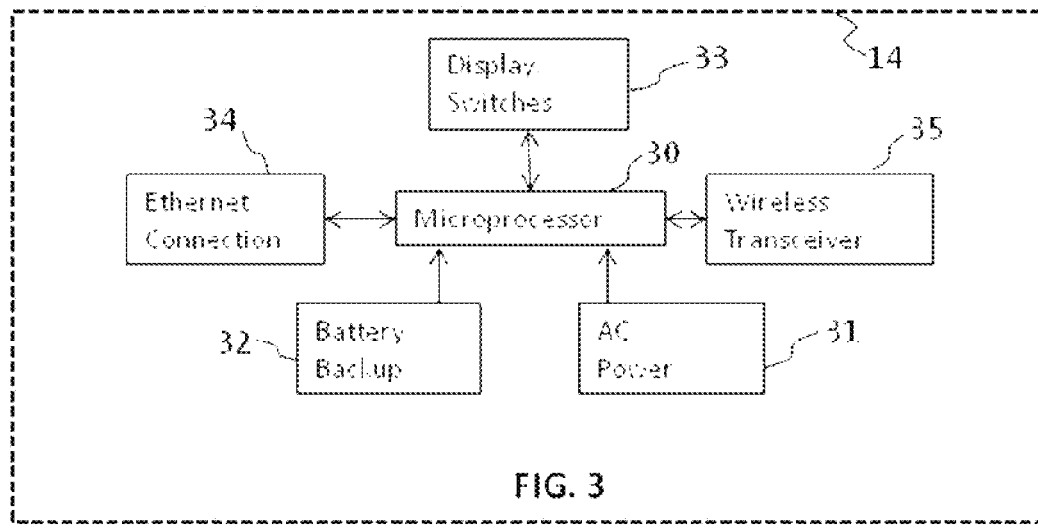
FIG. 3 illustrates one embodiment of a base station.

FIG. 3 illustrates an embodiment of a base station 14 that may include one or more microprocessors 30, a power source 31, a backup power source 32, one or more I/O devices 33, and various communications means, such as an Ethernet connection 34 and transceiver 35. The base station 14 may have more processing and storage capability than the detection unit 12, and may include a larger electronic display for displaying EMU signal graphs for a caregiver to review EMU signals in real-time as they are received from the detection unit 12 or historical EMG signals from memory. The base station 14 may process EMG signals and other data received from the detection unit 12. If the base station 14 determines that a seizure is likely occurring, it may send an alert to a caregiver via transceiver 35.

Various devices in the apparatus of FIGS. 1-3 may communicate with each other via wired or wireless communication. The system 10 may comprise a client-server or other architecture, and may allow communication via network 15. Of course, the system 10 may comprise more than one server and/or client. In other embodiments, the system 10 may comprise other types of network architecture, such as a peer-to-peer architecture, or any combination or hybrid thereof.

Figure 4:
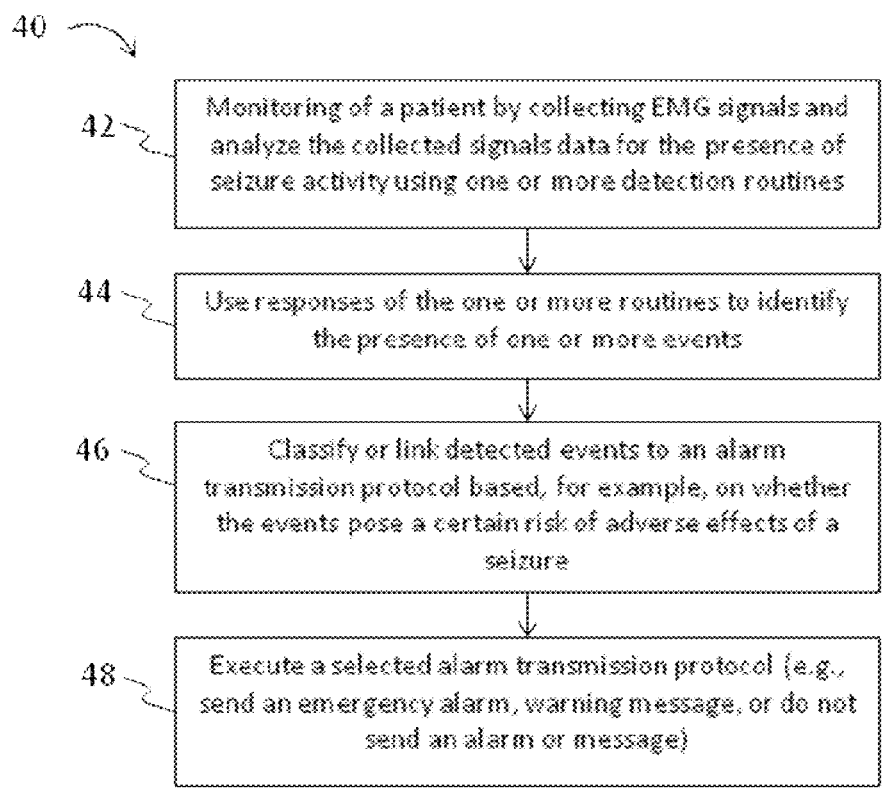
FIG. 4 illustrates one embodiment of a method for monitoring a patient for seizure related activity and selecting a protocol for alarm transmission.

FIG. 4 illustrates an exemplary embodiment of a method 40 of collecting EMG signals, processing the signals to detect seizure events, and execution of an alarm transmission protocol based on the detected event. Detected events may, for example, include identification of a part of a seizure or identification of more than one parts of a seizure. For example, identification of a clonic-phase part of a seizure may be treated as an event or identification of two or more temporally correlated parts of a seizure such as identification of a tonic phase part and identification of a clonic phase part of a seizure may be treated as an event. That is, the aforementioned detections may be considered detection of one tonic-clonic seizure event. In some embodiments, more than one routine may be executed in a monitoring protocol including routines configured for detection of different parts of seizure activity. For example, in some embodiments, a first routine may be configured to be responsive to tonic-phase seizure activity and a second routine may be selectively responsive for clonic-phase seizure activity. And, by combining outputs from various routines different events may be detected.

In the step 42, one or more EMG sensors may be used to monitor a patient for seizure activity by collecting EMG signals. In some embodiments, additional sensor data may also be collected and used to determine risk of adverse effects of detected seizure activity. Signal data may, for example, be collected and analyzed using any of the various routines as further described herein. In the step 44, based on the responses in the various executed detection routines, different detection events may be identified. For example, as shown in Table 1, various routines may give different output responses and based on those routine responses different events may be identified. In the step 46, detected events may be linked to one of several selectable alarm transmission protocols. That is, a specific alarm transmission protocol may be selected. The specific form of data determined for transmission may, for example, depend upon risk associated with a detected event. Data determined for transmission may, in some embodiments, take any of various forms including, for example, a form that includes any combination of an alarm message, subset of statistical information related to algorithm detection, as well as time and/or frequency domain EMG data. As shown in the step 48, a transmission protocol may then be executed, and if deemed to be warranted, appropriate data may be transmitted.

In some embodiments, one or more EMG sensors may be used to monitor the patient for seizure activity and EMG signals may be collected and analyzed for the presence of one or more characteristics of seizure activity. For example, the presence of a certain characteristic of seizure activity may be determined by analyzing collected EMG data using one or more analysis routines. And, in some embodiments, to facilitate risk stratification, at least one routine may be selective for activity of a particular part of seizure activity. A routine may be "selective" for a characteristic present in a part of a seizure and the characteristic may be detected as a positive response of the routine in a patient experiencing that part of a seizure (or when transitioning into that part), but the characteristic may be substantially absent, undetectable, or give a substantially different output response in the absence of that part of a seizure. And, the likelihood that a positive response to that routine (or combination of routines) should properly be associated with the presence of a certain part of a seizure may then be established. Therefore, execution of one or more selective routines may encourage identification of a particular part of a seizure and classification of a detected seizure may then be based on the presence or absence of that seizure part. Risk stratification may then be made accordingly if, for example, the presence of that part of a seizure is more or less associated with likelihood of a patient experiencing adverse effects of a seizure.

For example, in some embodiments, one routine may analyze EMG data for the presence of increased EMG amplitude or sustained increases in EMG amplitude and another routine may analyze EMG data for the presence of clonic-phase burst activity. More than one detection routine may run simultaneously, and in some embodiments, a detected event may be identified based on whether a certain portion of collected EMG signal data exhibits a positive response in one routine or exhibits a certain combination of responses in more than one routine. And, in some embodiments, a detected event may involve responses from one or more routines wherein the routine responses are separated in time. For example, two or more routine responses from EMG data collected at different times may be temporally correlated and may be treated as being associated with a single detected event as further discussed below. Or, if suitably separated in time, two or more routine responses may be deemed to be separate events, and those separate events may then, for example, be linked to separate event responses.

A routine for analysis of EMG signals with increased EMG amplitude may, for example, include collecting signals over some period of time and determining if the collected EMG signal amplitude or an integrated value of signal amplitude within one or more time windows within that period is elevated over a certain threshold. And, in some embodiments, based, for example, on a number of time windows in which a certain threshold amplitude was achieved it may be determined if a level of signal elevation was sustained for a threshold duration. Threshold levels of EMG signal amplitude may, in some embodiments, be set to make that routine responsive to even weak muscle motor manifestations. For example, in some embodiments, a threshold setting may be established based on a measurement of the maximum signal amplitude an individual may provide during a voluntary muscle contraction. For example, for some patients, a value of about 2% to about 50% of a maximum voluntary value may be selected to capture weak motor manifestations. Other thresholds may also be used, but raising thresholds too high may limit responsivity of the routine to some motor manifestations.

In some embodiments, signal amplitude may be scaled in units of standard deviation above a baseline signal. For example, an evaluation of whether sustained amplitude elevations are present may include scaling the difference between a measured signal amplitude and a baseline signal amplitude in units of standard deviations and assessment of whether the number of standard deviations exceeds a threshold value (or Z-factor) (in units of standard deviations) and/or exceeds that factor over a certain time interval. To be sustained a signal or smoothed signal value may be required to maintain a threshold level for at least a critical number of times in a time interval or may be required to maintain the threshold level over the entirety of the time interval. To improve the signal-to-noise ratio of a detected signal it may generally be desired to integrate the signal for a certain interval of time such as about 100 milliseconds to about 500 milliseconds. Selection of longer integration intervals may make the system less susceptible to random fluctuations and sources of signal noise and may improve overall detection sensitivity. Therefore, for some routines, including some routines responsive to weak motor manifestations and/or certain parts of tonic phase activity, it may be advantageous to integrate over windows of time that are relatively long such as, for example, by integration over windows of time on the order of hundreds of milliseconds.

However, integration of EMG signal over significant durations generally results in a loss of temporal resolution in the signal data, and routines designed to be selective for transient EMG activity typical of clonic-phase bursts (which may only last for a period of hundreds of milliseconds) may generally need to break up and measure EMG signal amplitude within shorter windows than used in other routines. For example, to determine if a signal fluctuates over an interval of time on the order of about a hundred milliseconds one needs to measure and analyze the signal at least some number of times over the time period of individual fluctuations. In some embodiments, a routine for detection of clonic-phase bursts may include identification of peaks and qualification of peaks that meet criterion to be qualified as clonic-phase bursts. For example, in some embodiments, EMG data may be sampled over various intervals suitable to detect the time variation of signal during a clonic-phase burst pattern. The data may be accessed using a peak detection program and then subject to qualification as may be used to determine if any identified peaks may be deemed clonic-phase bursts. For example, by selectively counting elevations qualified based on meeting minimum and/or maximum width requirements typical of clonic-phase activity an algorithm may be made selective for clonic-phase burst activity. That is, a routine suited for measurement of a characteristic of clonic-phase burst activity, such as clonic-phase burst count, may be configured to be selective for the clonic-phase of a seizure.

As described herein, by analysis of EMG data for signal elevations that meet minimum and/or maximum width requirements, a routine may be made selective for a pattern that is characteristic of clonic-phase activity. Moreover, because the clonic-phase of a seizure may be correlated with seizure risk, including such a routine, i.e., one that is selective for clonic-phase activity, may facilitate risk stratification. A more detailed description of some embodiments of routines selective for clonic-phase activity is included further herein and in the examples section at the end of this application. Those routines may be responsive when the clonic-phase of a seizure is present and/or may be responsive during periods that typically lead into the clonic-phase.

In some embodiments, the method 40 may include collecting and analyzing EMG signals (step 42) for seizure activity using a routine configured for measuring sustained EMG activity and with settings and/or thresholds suited to provide a positive routine response if tonic-phase seizure activity is present. Another routine may, in some embodiments, include settings and/or thresholds suited for selective detection of the clonic-phase of a seizure. That is, the routine may indicate a selective response if clonic-phase activity is present. In the step 44, a method 40 may then determine, based, for example, on data from either or both of the aforementioned routines whether a detected seizure event is present.

If, for example, a first routine is configured to be responsive to tonic-phase seizure activity and a second routine is selectively responsive for clonic-phase seizure activity, an EMG signal may, for example, when analyzed, initiate a positive first routine response, but may not initiate a positive second routine response. Those routine responses may be used to classify the EMG signal as corresponding with a tonic-phase detection event. In some embodiments, a first routine may be associated with threshold settings wherein a positive routine response may be used to detect an event that may correspond to either of a tonic-phase seizure or weak motor manifestation including manifestations that may not be related to a seizure. And, for some patients, such events may only carry minimal risk of adverse effects of a having a seizure and may be given a warning event status. For example, in some embodiments, isolated detection of weak motor manifestations or tonic-phase activity may only qualify an event as demanding a warning status and an associated warning transmission protocol may be selected.

In the step 46, it may be determined if transmission of EMG data or an event message is warranted. For example, an event may be assigned a warning status and may, in some embodiments, initiate a transmission protocol that sends a message that a warning event was identified. Such a message may, for example, be advantageously transmitted (as shown in step 48) using only minimal power consumption. The message may, in some embodiments, be limited to include a time stamp of the event and describe that a warning was reached or may include a description that a warning threshold was reached together with summary data including, for example, an amplitude value reached or how long a threshold value of amplitude was maintained. In other embodiments, more extensive EMG signal data may also be transmitted together with a warning message, but generally for events that pose only limited risk the extent of transmitted data may be limited.

A monitoring system may also initiate transmission of an emergency response such as may include, for example, an emergency message. For example, in some embodiments, each of the aforementioned routines (e.g., a first routine for increased or sustained activity and a second routine configured for transient EMG activity), may be responsive to an EMG signal collected during some collection time period and a detected EMG signal event may then be classified as associated with the presence of a clonic-phase portion of a seizure. That classification may, for example, initiate an emergency response message. That is, a detected clonic-phase event may be linked to alarm protocol that includes an emergency response. A clonic-phase event may also be deemed present if, for example, an EMG signal only responds to the second routine. To that point, a first routine may, in some embodiments, be responsive to tonic-phase activity, but may also respond to clonic-phase activity. However, lack of selectivity for that first routine may not prevent selective identification of seizure activity and classification based on the presence of either the tonic or clonic phase because such ambiguity may be resolved by consideration of the other routine. For example, because the second routine may be selective for clonic-phase activity, the second routine would not respond if only tonic-phase activity were present. Therefore, both tonic and clonic activity may, in some embodiments, be selectively detected.

Based on detection of clonic-phase activity, an event may be risk-stratified, and a suitable transmission protocol then be selected as shown in the step 46. For example, in some embodiments, a clonic-phase event may be deemed an emergency event and a transmission protocol may be selected such as may include an alarm message being directly sent to EMT personnel. An ambulance may then be sent to the patient's house or another appropriate emergency response may be made. For example, another caregiver may alternatively or additionally be contacted and instructed to locate and check on the patient. In some embodiments, detection of a clonic-phase event may initiate a transmission protocol in which time and/or frequency dependent data is remotely sent to a system user. The remote user may then be given an option to evaluate the data, and may execute an appropriate response such as may include terminating an emergency response or initiation of an emergency message, if a remote user is sent data and required to actively initiate an emergency message, that data may be considered part of a warning protocol, i.e., data or a message that still requires initiation by a user to raise the event to emergency status may be considered herein as part of a warning protocol. In some embodiments, a recipient may be sent data, but after some time period, the system may automatically route an emergency message to a caregiver. Therefore, some transmission protocols may be predetermined to initiate contact with a caregiver and may be considered to be part of an emergency protocol. And, as used herein, unless otherwise noted, an "emergency transmission protocol" may refer to a transmission protocol where an emergency message is sent or predetermined to be sent to a caregiver including, but not limited to an EMT caregiver, with instructions to physically assist the patient, e.g., to actively move to the patient's location. And, in some embodiments, an emergency protocol may still be interrupted and canceled by a remote user.

Continuing with the example of a first routine configured for identification of increased or sustained EMG activity and a second routine configured for identification of transient EMG activity, in some embodiments, classification and risk stratification for various detected events may be selected as shown in Table 1.

TABLE 1

| Event | Routine 1 - Status | Routine 2 - Status | Classification | Status/Transmission Protocol |
|---|---|---|---|---|
| A) | negative | negative | non-seizure | no transmission |
| B) | positive | negative | tonic-phase event or tonic/non-seizure event | warning protocol (automatic message only) |
| C) | negative | positive | clonic-phase event | emergency protocol (Que alarm message and send data - enable review of EMG data by a remote user and/or verification of event status) |
| D) | positive | positive | clonic-phase event | emergency status (automatic message along with EMG data to qualified individual) |

Table 1 shows an embodiment of how responses for routines may be combined and associated with seizure events, and may be applied for EMG data collected at about the same time; i.e., where each routine is applied to EMG data collected at about the same time. However, a monitoring system may also collect and analyze EMG signal using one or more routines that may be responsive to EMG signal data over time. And, for example, a routine or group of routines may respond to different portions of EMG signal separated in time. If the routine responses are derived from suitably isolated EMG data, the routine responses may be treated as corresponding to separate events. For example, in some embodiments, if two routine responses are associated with portions of EMG signal data that are separated in time from each other by greater than about 1 minute to about 10 minutes the two routine responses may be treated as being from isolated events. Individually detected events may be classified based on risk, and an appropriate transmission protocol linked to the event. Likewise, in some embodiments, if two routine responses are separated by less than a certain duration they may, for example, be deemed to be temporally related and considered together as one event. That is, the temporal relationship between two or more routine responses associated with different portions of signal data may be determined, and for example, the signal data may be deemed to be part of a multi-stage seizure event. For example, routine responses associated with each of a tonic phase and a clonic phase of a seizure may be deemed temporally related and treated to likely be the result of a single tonic-clonic seizure event. For example, in some embodiments, if the responses of one or more routines shows that a tonic phase is identified and if, within about 2 seconds to about 60 seconds after that identification is made, one or more routines show that a clonic phase is present a tonic-clonic seizure may be deemed likely. Detection of a tonic-clonic seizure event may then be treated as a single event for purposes of classification and risk-stratification. For example, a tonic-clonic event may, in some embodiments, be deemed to be an event that warrants execution of an emergency transmission protocol.

The systems herein may, in some embodiments, analyze collected EMG signals based on combinations of responses derived from individual routines. And, in some embodiments, a number of responses to signal data, including combinations of responses of multiple routines over multiple time intervals, may be considered when classifying detected data based on risk.

In some embodiments, if a number of routine responses are detected over time the system may, for example, execute one or more additional actions. For example, the system may execute an algorithm suited to evaluate intervening periods between positive routine responses and examine the intervening periods for signatures of different activity. In some embodiments, the amplitude of EMG data in intervening periods between positive routine responses may be analyzed for the presence of EMG signal that may be elevated, including, for example, signal that may be elevated yet still below a threshold level suitable to trigger a response in individual routines. And, for example, based on whether a certain EMG signal level is or is not reached within one or more intervening periods between the responses, an algorithm may treat a series of responses in different ways. For example, the responses may be treated as individual events or different algorithms may consider whether the individual responses are likely to be part of one or more multi-stage seizure events. And, in some embodiments, patterns of multi-stage seizures may be based on collected data for a certain patient or certain patient demographic.

In some embodiments, the amplitude of EMG data in intervening periods between positive routine responses may be analyzed for the presence of EMG signal that may be either elevated or depressed. For example, some patients may experience a series of seizure events and following those events they may experience a general state of central nervous system depression (CNS). That depression may be related to a high risk of SUDEP. And, if CNS depression follows a series of seizure events such may be particularly important to detect. And, some multi-stage algorithms may look for the presence of multiple events that pose a risk of SUDEP. In some embodiment, those algorithms may examine whether signal between routine responses meets any of various profiles that may reflect CNS depression. Such patterns may include the presence of a trend in relative signals for baseline periods between the responses. For example, variability and/or trends in the EMG data may be considered.

And in some embodiments, data from either of saturated oxygen levels or heart rate may also be considered. A change in heart rate or oxygen levels may be a particularly important consideration in determining the status of a patient. However, for some patients, a significant period of time with only minor suppression of heart rate may be present before rapid changes in heart rate during SUDEP. Likewise, oxygen saturation levels may change only slowly during the progression of SUDEP. Measurement of levels of carbon dioxide may be more diagnostic of the onset of SUDEP because those levels may change more rapidly during initial periods of SUDEP progression. However, measurement of carbon dioxide levels in an ambulatory setting may be difficult. And, by analyzing the above sensor elements together with EMG data detection of initial signatures of SUDEP may be improved. In some embodiments, EMG data may be used to trigger execution of or adjust one or more other sensor routines. For example, one or more responses may be used to trigger collection of data using a pulse oximeter or to adjust thresholds and sensitivity of responses based on heart rate and/or saturated oxygen levels. And, trends or variability in pulse oximeter data may then be considered in determining an overall response to the available set of data. For example, in some embodiments, an emergency event or several suitable warning events related by some intervening time interval may be used to trigger collection of data using one or more additional sensors including a pulse oximeter.

In some embodiments, if over a certain time period, one or more responses, including, for example, positive responses that may individually be deemed warning events, are detected, an appropriate message may be sent to a remote user informing the user of the presence of the one or more responses. The remote user may then, for example, be able to request that additional EMG information is transmitted such as, for example, transmission of data that may be used to display the time and/or frequency dependence of relevant EMG signals. In addition, the user may initiate any of various calibration procedures or other procedures as may be useful to further evaluate the collected EMG signal data and/or the state of sensors during a certain time period. Other appropriate actions may also be taken including calling the patient or another caregiver. In some embodiments, a monitoring system may treat a series of responses in a manner that may depend upon whether the system is in one of several different selectable states. For example, a patient may be given an option to select one or more different monitoring settings based, for example, on whether the patient is in bed sleeping, whether the patient is at home alone, or if the patient is at home with another person. And, depending on whether the patient is in one or another of those states, for a certain response or group of responses, a monitoring system may, for example, select a transmission protocol associated with either a warning of emergency status.

The method 40 may be useful in organizing whether, for a certain event, it is desirable to transmit detected data and/or what form the transmitted data may take. For example, a transmission protocol may be selected that only sends a message of the patient status (and not bandwidth intensive time and/or frequency domain EMG data), and a remote user may be given the option to further analyze and review EMG data and discount the data or take one or more other actions as described herein. Importantly, at least for some detected events, that analysis may take place before an emergency message is transmitted. For example, in some embodiments, further analysis or review may be required before an emergency message is sent or review may be enabled because an automatic alarm message is queued for transmission but not immediately sent. Because some patients with epilepsy may tend to trigger responses from non-seizure or weak events more or less often and since the cost and/or inconvenience of initiating an inappropriate response to an event may be substantial, risk stratification of events and review of events, including those that may be difficult to access, may be highly desired. In addition, in some embodiments, analysis and review of data may be made without manual intervention by a remote user.

For example, in some embodiments, in addition or alternatively to execution of a warning transmission protocol, detection of a warning event may automatically initiate further analysis and review of collected EMG data based on application of one or more algorithms, including, for example, algorithms that examine sensors for proper calibration and/or for proper surface contact integrity with skin. And, that analysis and review may, in some embodiments, be initiated by either or both of a remote user and/or by the detection system automatically. In addition to EMG data associated with one or more detected event, that further analysis may include processing of EMG data that was collected prior to a detected event and/or after the detected event.

In some embodiments, in response to a detected event, a period for further EMG collection may be triggered. At the completion of the period or at some other time during the period, one or more algorithms may be executed that again considers the status of the patient. For example, in response to some events, a warning period of further analysis may be triggered. At the end of a warning period, a selected algorithm may direct the system to either initiate a transmission protocol or clear the warning status and return monitoring to a standard measurement protocol. Importantly, at the time of warning period completion, the system may have access to both the event that triggered the warning period and further collected EMG data and may consider all of the available data to determine an appropriate response. Execution of a warning period may, in some embodiments, be triggered in response to a warning event and may be executed alternatively or additionally to execution of a warning transmission protocol as described in the method 40.

For example, an event suitable to initiate a warning may be detected, and a monitoring system may then continue monitoring the patient and collect further information to more fully evaluate the state of the patient. Upon further evaluation, one or more routines may be responsive to further collected EMG signal and another event (e.g., an event that changes the status of the patient) may be detected. Ideally, that event may be detected with greater certainty than the initial warning event. And, therefore, by waiting until a more certain event detection, the system may determine a more appropriate response for the patient.

In addition, in some embodiments, other routines may be triggered to specifically probe data for signatures of non-seizure activity and such data routines may be used to avoid false positive detections by discounting the significance of a warning event. In some embodiments, dedicated routines that negatively weight EMG data, including, for example, one or more periodicity routines that look for artificially periodic or regular signals, may be triggered when a warning period is initiated. Other routines that may negatively weight EMG data may include comparison of data to a non-seizure waveform. For example, comparison of EMG waveform data to a database of other spectral profiles (e.g., model profiles for seizures and/or non-seizure events that may be patient specific) may be executed and this information may be used to discount a warning event. In some embodiments, it may be beneficial to execute at least some routines at a base station. Therefore, in some embodiments, a response to detection of a warning event may be the sending of data to a base station.

Some of the embodiments described herein that include instructions for further characterization of warning events, may include one or more routines that are highly sensitive for even weak motor manifestations. And, for example, by including those routines and instructions, some patients, including some patients that are particularly difficult to monitor, may be successfully monitored in an ambulatory setting. For example, for some patients that may have significant levels of adipose tissue, it may be difficult to discriminate seizure activity from non-seizure activity. And, for those patients, it may be difficult to set thresholds based on EMG amplitude or sustained EMG amplitude that fully discriminate seizure event data from non-seizure events. To alleviate that concern, it may be desirable to collect further information after a warning event such as may be executed to more fully evaluate the event, and after that further evaluation an emergency alarm may be initiated if a dangerous event was suspected to have occurred.

In some embodiments, methods of detection may include execution of one routine (or group of routines) that analyzes EMG data for the presence of clonic-phase bursts and further include execution of another routine suitable to detect initial or weak motor manifestations. Those embodiments may include instructions wherein if a routine suited for detection of weak motor manifestations is detected a warning flag may be tripped and a warning period may be established. Within the warning period, additional EMG may be collected. And, for example, the EMG signal may be analyzed for signatures of clonic-phase activity. If clonic-phase activity is detected during the warning period, then an alarm may be immediately executed. In some embodiments, such as when extended periods of elevated EMG activity are found in the warning period or where the warning signal does not attenuate, with or without the presence of clonic-phase activity, a response may be initiated. For example, in some embodiments, if motor components of general seizure activity are detected and elevated EMG amplitude exists for at least about 15 to about 30 seconds an alarm may be initiated even without detection of clonic-phase activity. In some embodiments, a method may, even if seizure or clonic-phase seizure activity is detected during a warning period, delay triggering of an alarm. For example, the warning period may run to completion and only after the warning period terminates may an alarm be initiated. For example, a method may wait until the end of the warning period to collect further data and increase confidence that the emergency alarm is proper to send. In addition, within a warning period, another event may be detected that qualifies the detection to likely be a false positive detection. For example, a routine may be triggered that indicates that the sensor may have lost calibration or it may be determined that the signal is artificially periodic and likely to be from non-seizure sources.

As noted above, within the time period of triggering of a warning state the EMG data may be further characterized, e.g., clonic-phase EMG data may be detected or routines may specifically discount a warning trigger. Decisions based on a warning threshold detection may also, in some embodiments, be linked to detection of other corroborating data including data collected by other sensors such as implanted or others sensors that may provide information about the physiological state of the patient. Alternatively, after a warning time period is triggered, the threshold event triggering the period may have not yet been further characterized. In the event that a first threshold event is not yet further characterized, the method may then initiate a response based on the available collected data. For example, an emergency response may be triggered or some other response may be made. Decisions based on those first threshold detections may, as discussed above, be patient-specific or may be state specific. For example, a patient who is deemed to be at high risk for adverse consequences from weak seizure events may be treated differently than another patient deemed to be at a lower risk. Or, a patient who is home alone or sleeping may be treated differently from a patient known to be in the presence of another person or caregiver.

Figure 5:
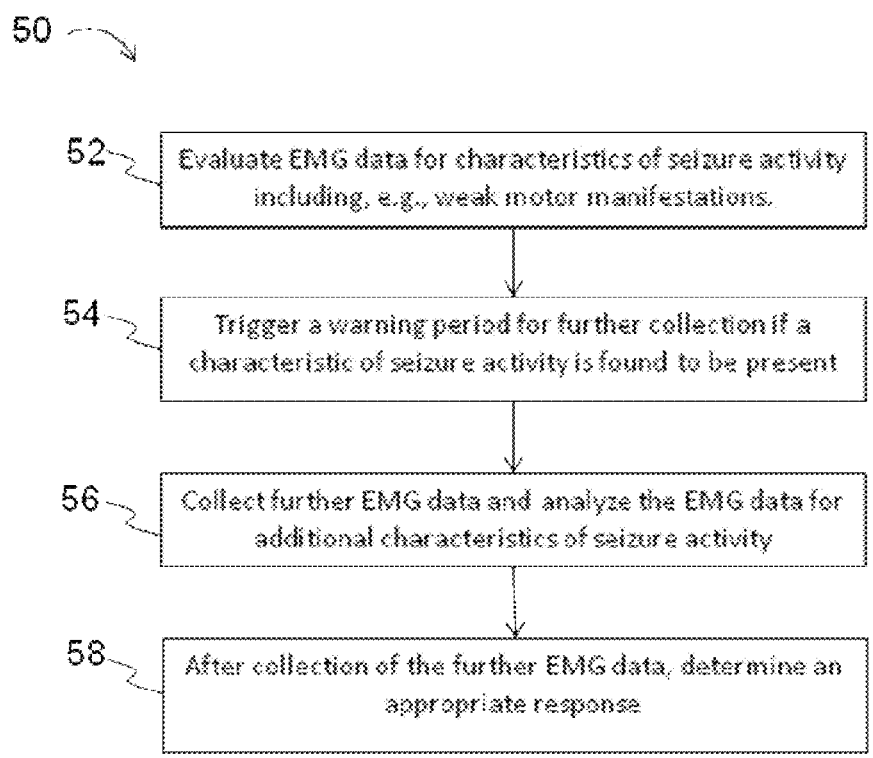
FIG. 5 illustrates another embodiment of a method for monitoring a patient for seizure related activity.

An exemplary embodiment of an embodiment of a method 50 in which a warning period may be established is shown in FIG. 5. As shown in the step 52, EMG data may be collected and analyzed for the presence of characteristic of seizure activity. For example, a routine may be configured to detect sustained EMG signal amplitude which may be characteristics of seizure activity, and may, in some embodiments, include threshold settings that make the routine highly sensitive to even weak muscle motor manifestations. If upon execution of the routine, a positive response is determined, a warning flag may be tripped. For example, tripping the warning flag may start a timer defining a warning period. A warning period may, for example, be configured to last for a period of time suitable to further evaluate EMG data. A warning period may, for example, in some embodiments, last for about 15 seconds to about 30 seconds. As shown in the step 56, further EMG data may be collected during the warning period as may be used to analyze the collected EMG data for additional signatures of seizure activity. In some embodiments, at least one routine applied to analyze that further EMG data may be responsive to clonic-phase seizure activity. At the end of the warning period, an appropriate response may then be executed.

In some embodiments, a routine may be selective for clonic-phase seizure activity and may include collecting EMG signal and evaluation of the EMG signal data for the presence of transient EMG signal elevations or bursts. Methods for identifying bursts and for collection and counting of bursts are further described herein and in Applicant's U.S. patent application Ser. No. 13/275,309 and Applicant's Provisional Patent Application 61/969,660. And, for example, the routines therein for detection of seizures, including, for example, those that determine either burst activity, burst count, or the presence of a burst train, may be applied as a routine that may be selective for clonic-phase burst activity and selectively related to clonic-phase activity. In addition, some of the routines therein may describe a supervisory algorithm wherein the input of different routines may be weighted and used to determine if a seizure is present. And, by suitably weighting individual routines based on clonic-phase burst activity a supervisory algorithm may be made more or less selective for the clonic phase of a seizure. Therefore, the output of a supervisory algorithm as described therein may also be used, in some embodiments, as a routine that may be selective for the presence of clonic-phase activity.

As described therein, EMG signal data that meets various requirements or thresholds may be qualified to be a clonic-phase burst. For example, a clonic-phase burst may be qualified based on minimum and/or maximum width requirements. Processing operations such as signal rectification, filtering, and/or other processing operations may be executed as may be appropriate to identify clonic-phase burst data and determine a clonic-phase burst count. For example, an analysis routine may include a peak detection program, which, for example, after band-pass filtering and rectification may identify and shape data. Once processed, generation of burst statistics, comparison to thresholds, and qualification of data may be more readily accomplished. Any suitable peak detection technique may be used (e.g., continuous wavelet transform). For example, in some embodiments, peak detection may include data smoothing techniques (e.g., moving average filter. Savitzky-Golay filter, Gaussian filter, Kaiser Window, various wavelet transforms, and the like), baseline correction processes (e.g., monotone minimum, linear interpolation, Loss normalization, moving average of minima, and the like) and application of one or more peak-finding criteria (SNR, detection/intensity threshold, slopes of peaks, local maximum, shape ratio, ridge lines, model-based criterion, peak width, and the like).

In some embodiments, peaks may be qualified against properties associated with the clonic-phase of a seizure or properties associated with a transition to a clonic-phase of a seizure such as may occur when tonic activity transitions into a clonic portion of a seizure. Peaks may, for example, be qualified based on an associated waveform, regularity, periodicity, width (which may be referred to as a duration width), amplitude, or other factors. Qualification may facilitate differentiation of seizures from non-seizure events and increase confidence that detected signal elevations are properly associated with seizure activity. And because other sources of EMG signal elevations (e.g., background interference, noise, and non-seizure movements) may be differentiated from qualified burst activity, monitoring EMG signals for that activity provides for high sensitivity detection of seizures.

In some embodiments, a portion of EMG signal may be transformed to the frequency domain and analyzed for the presence of clonic-phase burst activity. For example, using a frequency transform collected signal data may be converted to the frequency domain and the integrated intensity of signal within one or more frequency bands may be calculated for a given time period. And, by repeating that treatment over adjacent time periods one may analyze EMG signal data for data features that meet temporal width requirements associated with clonic-phase burst data. Alternatively appropriate bandpass filters may be used to isolate activity in one or more bands. For example, in some embodiments, signal within one or more bands ranging from about 2 Hz to about 120 Hz or about 240 Hz may be isolated and analyzed for the presence of clonic-phase bursts. And, at least for some patients, specific frequency bands may be selected that encourage differentiation of seizure events from non-seizure sources. Alternatively. EMG signal associated with all collected frequencies may analyzed for the presence of clonic-phase bursts, and collected EMG signal data may, for example, be analyzed without execution of a frequency transform.

In some embodiments, identified peaks may, as further described herein, be qualified against one or more properties typically present in the clonic-phase of a seizure, and may be qualified to increase selectivity for detection of the clonic-phase of a seizure. Peaks may, for example, be qualified based on an associated waveform, regularity, periodicity, width (which may be referred to as a duration width), amplitude, or other factors described herein. And, by selection of thresholds that excludes activity from other parts of a seizure, a routine may, for example, be made selective for the clonic-phase of a seizure. And, because non-seizure sources and other sources of noise may also be discriminated from qualified peaks, qualification of peak data may not only facilitate selective identification of the clonic-phase, but also enhance discrimination of burst data from non-seizure sources, and therefore, may be used to enhance overall system performance for seizure detection.

In some embodiments, regions of elevation of EMG signal amplitude may be qualified as meeting one or more conditions related to the duration of a signal elevation. That is, region of signal elevation or elevation over background by at least a SNR may be qualified as maintaining a requisite condition for a minimum duration, maximum duration or both.

For example, in some embodiments, to qualify signal data as suitable for clonic-phase burst identification, analysis of burst statistics, and or counting of bursts, signal data may be qualified based on fulfilling of a minimum burst width and/or maximum burst width criterion, and if some number of bursts is detected over some period of time a positive response may be logged. That is, a routine may count clonic-phase bursts or determine a clonic-phase burst rate and if the number or rate exceeds a threshold a positive response may be logged. In some embodiments, a burst envelope may be generated and the burst envelope may impact a SNR threshold that may be used to identify bursts. For example, with a simple peak detect method, clonic-phase bursts may be qualified by meeting a threshold SNR of about 1.25 to about 20 and by meeting a minimum threshold for burst width of about 25 to about 75 milliseconds and maximum burst width threshold of no greater than about 250 milliseconds to about 400 milliseconds. Clonic-phase burst may then be counted and a number of bursts or rate of bursts may be determined. For example, a positive routine response may then, for some patients, be triggered if between about 2 to about 6 clonic-phase bursts are measured within a time window of about 1 second or if another suitable number of clonic-phase bursts are counted in some other appropriate time window.

In some embodiments, positive routine response may be made if at least about 2 to about 6 clonic-phase bursts are measured within a time window of about 2 to about 5 seconds. A threshold number of clonic-phase burst count for a patient may be the same or different than an expected number of physiological events that may produce clonic-phase bursts. For example, depending on a SNR threshold level and or other thresholds at least some of the physiological events associated bursts may not be detected, but a threshold number of clonic-phase bursts may still be detected and may be used to trigger a positive routine response.

To further qualify signal data, other properties of clonic-phase activity, e.g., in addition to minimum and/or maximum widths of duration, may, in some embodiments, also be included in evaluation of EMG data. For example, in some embodiments, a portion of EMG signal may be identified to include one or more suspected bursts, and the portion of EMG signal may be transformed to the frequency domain and analyzed for the presence of frequency characteristics associated with clonic-phase activity. That is, frequency data may be compared to a model frequency waveform typical of clonic-phase activity. If the comparison does not support a finding that the frequency data may be associated with clonic-phase activity, the suspected bursts may, for example, not be included in the burst count characteristic. That is, the identified activity may fail qualification and may not be counted. Model waveforms may be based on EMG data for a particular patient or for a patient demographic, and in some embodiments, waveform data may be updated as historical EMG data is collected.

In some embodiments, regions identified as likely clonic-phase bursts may be further qualified based on additional criteria. For example, identified data, e.g., likely clonic-phase bursts, may be further analyzed based on one or more characteristic including periodicity, amplitude regularity, waveform regularity, other criteria described herein and combinations thereof. For example, in some embodiments, if identified data is determined to be artificially periodic the data may fail qualification and may not be then counted. Upon suitable qualification as meeting criteria of clonic-phase activity, clonic-phase burst count may, for example, be used, to evaluate whether seizure activity or the clonic-phase of a seizure is present.

In some embodiments, for example, to be further qualified as a clonic-phase burst, identified data, e.g., meeting the above minimum and/or maximum duration requirements, may include an adjacent period of substantially quiet signal, the quiet period lasting for a duration of about 50 milliseconds to about 300 milliseconds. That is, the presence of an adjacent quiet period of threshold duration may be used to qualify a burst as related to clonic-phase activity. Upon final qualification as meeting criteria of clonic-phase activity, clonic-phase burst count may be used to evaluate whether seizure activity or the clonic-phase of a seizure is present. For example, a positive routine response may then, for some patients, be triggered if between about 2 to about 6 clonic-phase bursts are measured within a time window of about 1 second or if another suitable number of clonic-phase bursts are counted in some other appropriate time window.

In some embodiments, identified data as likely derived from clonic-phase activity may be further determined to be a burst train. A burst train may include any number of bursts that are temporally related to each other (present in a certain time window) and that may be pooled together to generate burst statistics and/or to look at trends in burst data over time. For example, a burst train may include a number of bursts such as about 3 to about 30. A burst train may include any portion of the total number of bursts present in the clonic-phase of a seizure. For example, a number of bursts selected to be included in a burst train may be made as appropriate to focus on one portion of the clonic-phase of a seizure such as the start of the clonic-phase. To that point, a burst train or burst included therein may (as described further in relation to FIG. 10 and routine 130) be qualified based on a distribution of time periods between individual bursts of the burst train and whether the distribution is typical of seizure or non-seizure activity. That is, a metric (such as e.g., standard deviation or average percentage deviation) related to the distribution of time periods between bursts may be calculated and used to qualify a burst train or bursts included in the burst train. If too great a number of bursts are included in a burst train then the metric may be high because the time period over which the burst train is measured may extend over a time frame where the average length of the time periods between bursts has increased. And, in some embodiments, bursts may be collected from each of a front, middle, and back portion of the clonic-phase of a seizure. And, in some embodiments, to determine statistics, such as may be used to identify a standard deviation or other burst statistics, a pooled value (based on data from each portion) may then be calculated.

In some embodiments, to be further qualified as a clonic-phase burst train, a qualified burst train, e.g., a number of nearby individual burst members of which may meet the above minimum and/or maximum duration requirements, may meet a threshold level for percentage burst deviation for the periods between individual bursts of the train. The presence of one or more clonic-phase burst trains may be used to detect seizure activity, initiate execution of an alarm or log a positive response in a routine.

Figure 6:
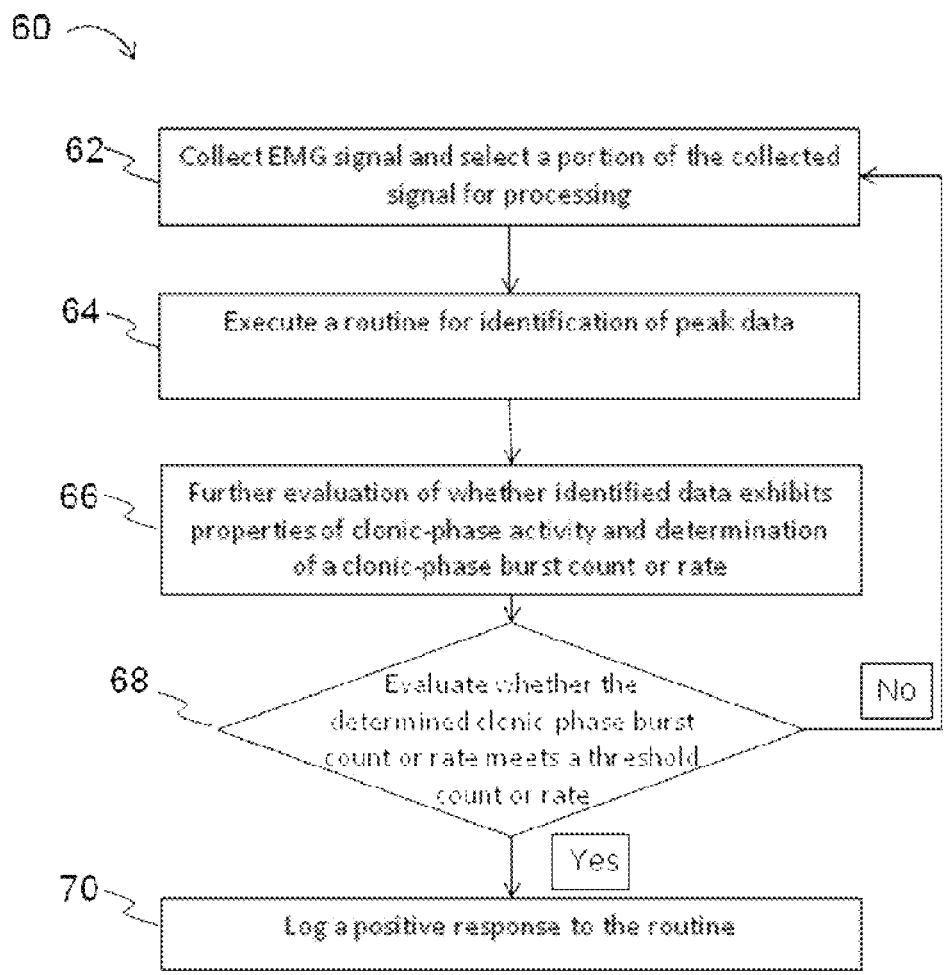
FIG. 6 illustrates an embodiment of a routine for analysis of EMG signal for seizure activity.

More generally, any number of steps of identification of suspected clonic-phase burst data and qualification of that data to increase the confidence that the data should properly be associated with the clonic-phase may be made. FIG. 6 illustrates an exemplary embodiment of a routine 60 of monitoring EMG data for characteristics of seizure activity including burst identification, and which may be used to initiate a response. That response may be used individually as a method of monitoring a patient or may be used in combination with other routines to more fully characterize a seizure and to execute risk stratification. In the routine 60, peak data may be identified and qualified in one or more steps to produce a value (such as clonic-phase burst count, clonic-phase burst count rate or other clonic-phase burst statistics), and that value may be compared directly to a threshold value (such as count, rate or other statistics threshold) and used to initiate a positive response in the routine. And, for example, if used individually as a method of monitoring, a positive response in the routine 60 may be used to directly trigger one or more transmission protocols.

In the step 62 of the method 60, an EMG signal may be collected and a portion of the collected signal may be selected for processing. In the step 64 one or more routines may be executed to identify if peaks are present in the selected data. For example, any of the routines 72 (FIG. 7), 96 (FIG. 8), and 120 (FIG. 9) or combinations of those routines may be executed. As shown in the step 66, in some embodiments, the routine 60 may include further evaluation of whether identified regions meet one or more properties associated with the clonic-phase of a seizure, and depending upon how many of the identified features meet qualification, a clonic-phase burst count may be determined. In the step 68, the determined burst count or rate may be compared to a threshold value. And, in the step 70, if the threshold value is met a positive response may be logged for the routine or an alarm may be executed. After a positive response is logged the system may, for example, then collect a next signal sample. More generally, EMG data may meet an initial screen to be identified, and any number of different properties may be compared to the identified data and may be used to qualify or further qualify the data as related to clonic-phase activity. When qualified, clonic-phase burst count may serve as a highly sensitive and selective seizure variable to analyze EMG data for the presence of seizure activity or for a clonic-phase portion of a seizure.

In some embodiments, as explained in further detail in the routines 72 (FIG. 7) and 96 (FIG. 8), a step 64 of method 60 may involve identification of EMG data that includes periods of short-lived elevations of EMG amplitude and which is a candidate for further qualification, e.g., further qualification as exhibiting clonic-phase behavior. For example, as further explained in step 90 of the more detailed routine 72 (FIG. 7), data may be qualified as including amplified signal that is maintained for a minimum threshold duration. Likewise, as further explained in step 110 of routine 96 (FIG. 8), data may be qualified as including amplified signal that is maintained for no longer than a maximum threshold duration. Based on the above criteria, EMG signal may be identified as likely including one or more clonic-phase bursts or series of clonic-phase bursts, and depending, for example, on the selection of above minimum and/or maximum threshold levels of duration, the identified signal may, at least for some patients, be highly selective for clonic-phase activity. For example, the identified EMG signal data may be suitably qualified, e.g., based on suitable minimum and/or maximum duration thresholds, that the data is likely to correlate with clonic-phase activity and may be directly incorporated into an algorithm for identification of seizure activity. For example, short-lived elevations or bursts may be counted and the burst count compared to a threshold count for evaluating whether a seizure or clonic-phase part of a seizure is present.

Figure 7:
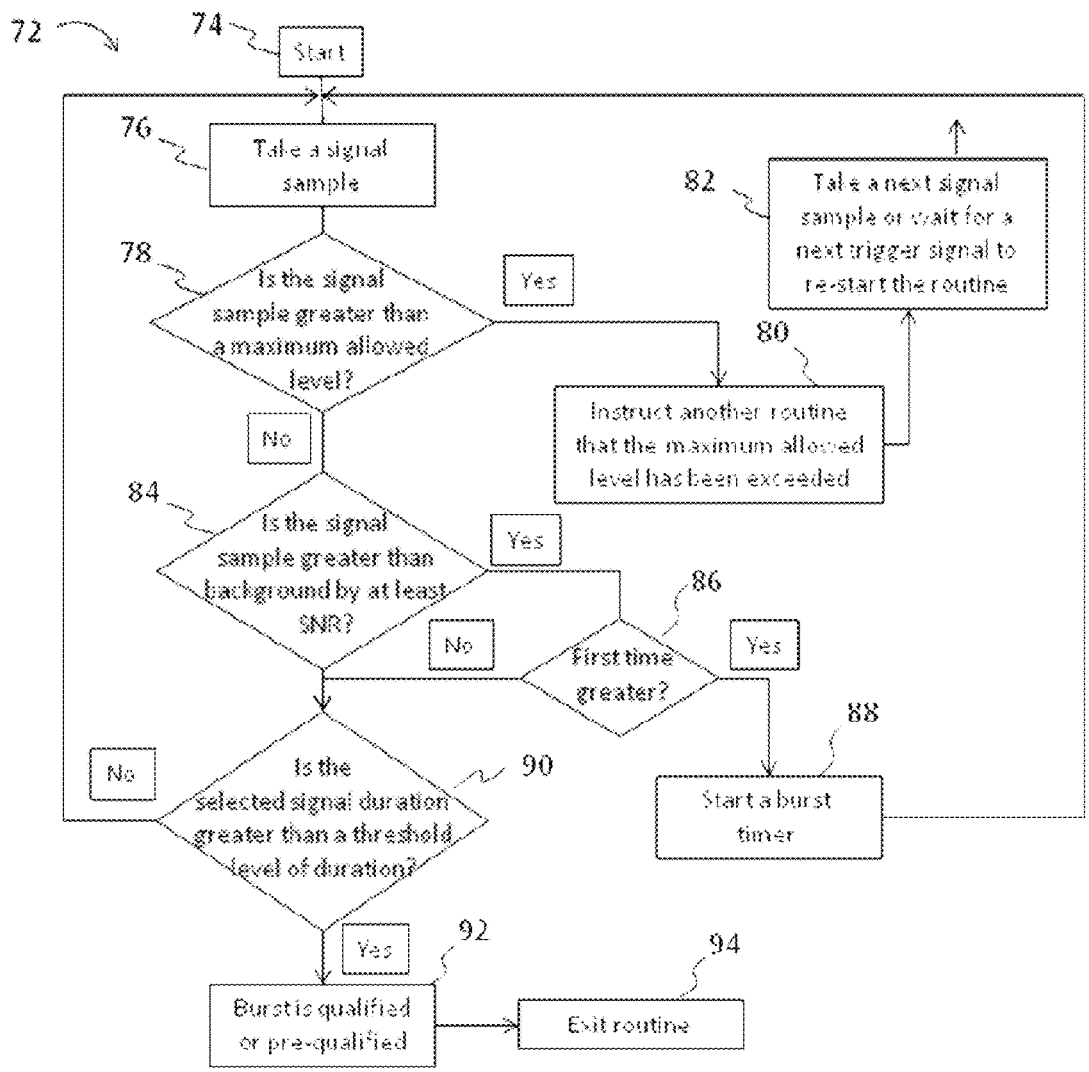
FIG. 7 illustrates an embodiment of a routine for analysis of EMG signal for seizure activity based on the detection of signal bursts.

FIG. 7 illustrates one embodiment of a clonic-phase burst identification routine 66 that may be used individually or in combination with another routine to identify a portion of signal data that may include clonic-phase bursts. The routine 72 is shown to include a start trigger 74. The start trigger 74 may, for example, be set based on a detected signal change or change with respect to background noise. The start trigger 74 may alternatively be set to start on predetermined intervals such as may be driven by a suitable clock routine. In the step 76, a signal portion may be selected for analysis. The signal portion may include any number of data points collected by an EMG sensor. In the step 78, the routine 72 may establish whether signal selected for analysis is above a maximum allowed value or threshold setting. For example, it may be desirable, at least in some routines, to determine whether the signal is inappropriately high or achieves a level that is unlikely to correspond with actual seizure activity, but rather may correspond, for example, to an artifact such as may be present if a sensor or sensor contact has become unstable or if the detection device is in need of calibration. In the step 80, another routine may be instructed that the signal has exceeded the maximum allowed value. The other routine may, for example, be a supervisory algorithm associated with an alarm decision or a routine organized to trigger recalibration of a detection unit or the routine that is looking for too regular a signal to be humanly produceable. As shown in the step 82, the routine 72 may then include taking a next signal sample or waiting for a next trigger to re-start the flow shown for the routine 72.

In the step 84 (which may additionally or alternatively be included to execution of the step 78), the routine 66 may determine if the selected signal sample's SNR is greater than a selected threshold. If the signal's SNR is greater than background by at least the SNR threshold, the routine 72 may determine (as shown in the step 86) whether the selected signal sample's SNR has exceeded the SNR threshold for the first time within the routine 72. If the signal sample's SNR was greater than the SNR threshold for the first time in the routine, a burst timer may be initiated as shown in the step 88. A burst timer may establish a threshold level for burst duration as may be useful, for example, to prevent transient spikes of activity (e.g., data spikes that may not reflect actual seizures) from being qualified as clonic-bursts. For example, the burst timer may run for a period of about 25 to about 100 milliseconds or some other suitable value that is shorter than typical of a burst of data originating from seizure activity. Following a start of a burst timer the routine 72 may take another signal sample and other steps of the routine may be initiated. In addition, appropriate flags may also be tripped such that next signals samples evaluated for signal and/or SNR levels are known to include preceding iterations of sample selection. For example, a second sample of data may be selected (step 76) and the selected signal may pass again through steps of the routine 72. If in the step 84 the selected signal (which may, for example, include data from several iterations of taking of signal sample), does not meet a threshold SNR, then a step 90 may be executed. In the step 90, it may be determined if the time period for the selected signal has exceeded a threshold duration level and if the duration level has been exceeded, then the selected signal may be qualified as a clonic-burst (step 92). Upon qualification of a clonic-burst the routine 72 may be exited.

Upon exiting of the routine 72, data may, for example, be further qualified for clonic-phase burst characteristics and/or may be passed to a routine that may evaluate the data to determine an appropriate response to the detected of burst data. For example, signal qualified in the routine 72 may exit the routine if it exceeds a threshold SNR for a threshold level of duration and it may, in some embodiments, be useful to determine if the signal also does not exceed a maximum threshold duration. To evaluate whether the exiting signal does not exceed a maximum threshold duration, the signal exiting the routine 72 may, for example, be sent to the routine 96 of FIG. 8. Also by way of example, burst data may be sent to a circular buffer that is periodically evaluated for the detection of a burst train or each time a burst is detected a determination may be made of whether or not to trigger an alarm. If in the step 90, the selected signal does not exceed a threshold signal duration, it may be deemed that the signal data is too short to qualify as a burst, and the routine may collect a next signal sample—clearing any appropriate flags—such as may have been tripped previously. Alternatively to collecting a next signal sample. EMG data may be collected and only if a next trigger is established may the routine 72 be re-initiated.

Figure 8:
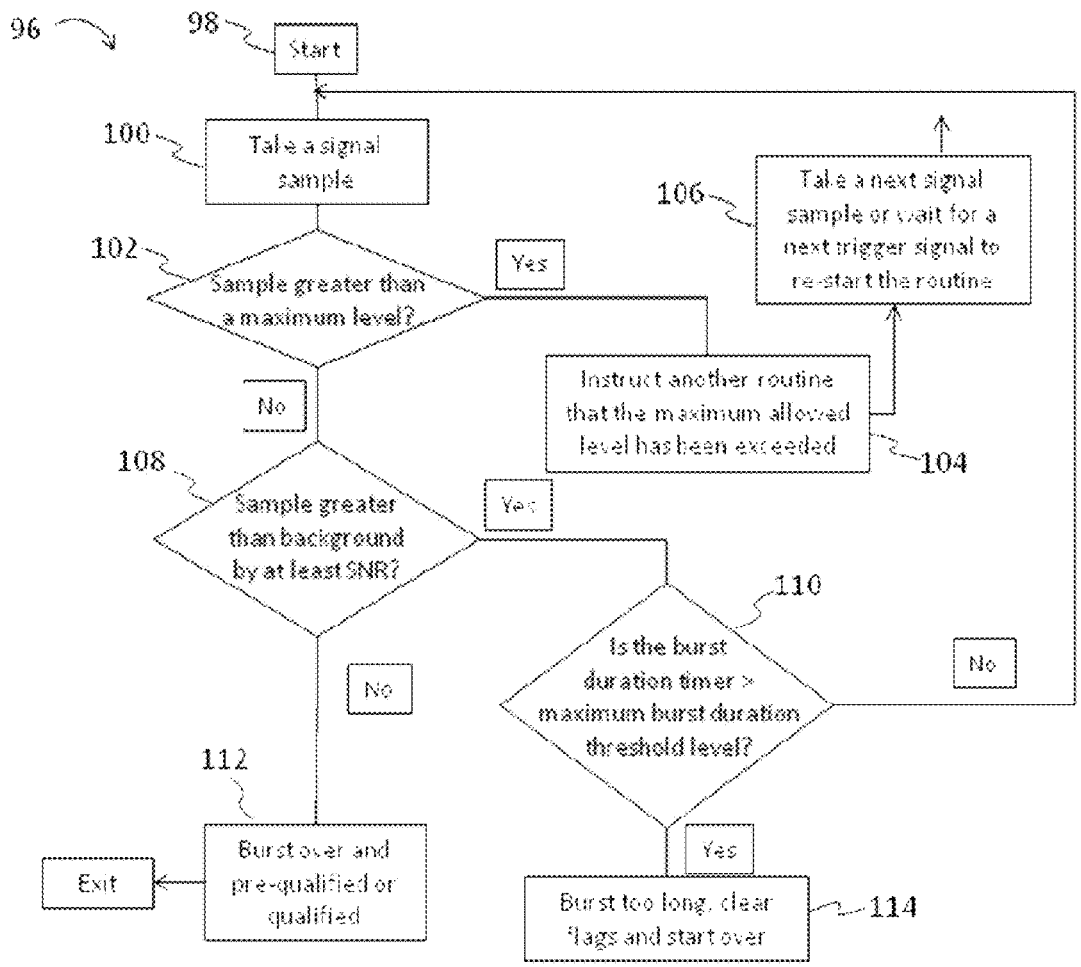
FIG. 8 illustrates another embodiment of a routine for analysis of EMG signal for seizure activity based on the detection of signal bursts.

FIG. 8 illustrates another embodiment of a burst detection routine 96 that may also be used individually or in combination with another burst detection routine to identify a portion of signal data that may include bursts. For example, when used in combination with the routine 72, the routine 96 may facilitate selection of bursts that meet each of a minimum and a maximum width criterion. Tailoring threshold levels of burst duration in the routines 72, 96 may, for example, include the selection of regions of EMG data that are elevated over a background level and maintain an elevated level for between about 25 to about 400 milliseconds. In the routine 96, a start signal (step 98) may, for example, be executed based on a detected signal change or change in signal with respect to a background level. A start trigger may alternatively be set to start on a predetermined interval such as may be established by a suitable clock routine. In some embodiments, routine 96 may automatically start once a pre-qualified burst is found in another burst detection routine such as the routine 72 as described in FIG. 7, and may be used to further qualify data also processed in the routine 72.

The routine may 96 may include taking a signal sample as shown in the step 100. In some embodiments, the routine 96 may include the step 102 wherein the routine may determine if the sample is greater than a maximum allowed level. If the maximum level is exceeded the method may instruct another routine as shown in the step 104, and in the step 106 a next signal sample may be taken or the method may wait for a next trigger before starting over. Alternatively or additionally to the step 102, method 96 may include step 108 which may include determining if the sample is greater than background by at least a SNR. If the sample signal is greater than background by at least the SNR, method 96 may execute the step 110. In the step 110, the method 96 may determine if a burst duration timer is greater than a maximum burst duration level. If routine 96 is executed in combination with the routine 72, the burst timer may have been previously tripped as described, for example, in the step 86 of the method 72. Alternatively, if, for example, routine 96 is executed separate of the routine 72 then a separate burst timer may have been triggered in other steps (not shown).

If the maximum burst duration threshold is exceeded, it may be deemed, as shown in the step 114, that a burst is too long to be indicative of a seizure. Appropriate flags may be cleared, and the process may start over by collecting a next signal sample or waiting for an appropriate trigger to re-start the process. If in the step 108, it is determined that this sample does not exceed the background by the SNR threshold level, a burst may be deemed to be over and the burst may be qualified a shown in the step 112. As further indicated in the step 112, the signal qualified as a burst may, for example, in some embodiments, be characterized by a certainty value, the center of the burst may be determined and the burst data may be written into a circular buffer for further analysis. Upon exiting of the routine 96, data may, for example, be further qualified for burst characteristics and/or may be passed to a routine that may evaluate a response to the detection of burst data. For example, burst data may be sent to a circular buffer that is periodically evaluated for the detection of a burst train or each time a burst is detected a determination may be made of whether or not to trigger an alarm.

Figure 9:
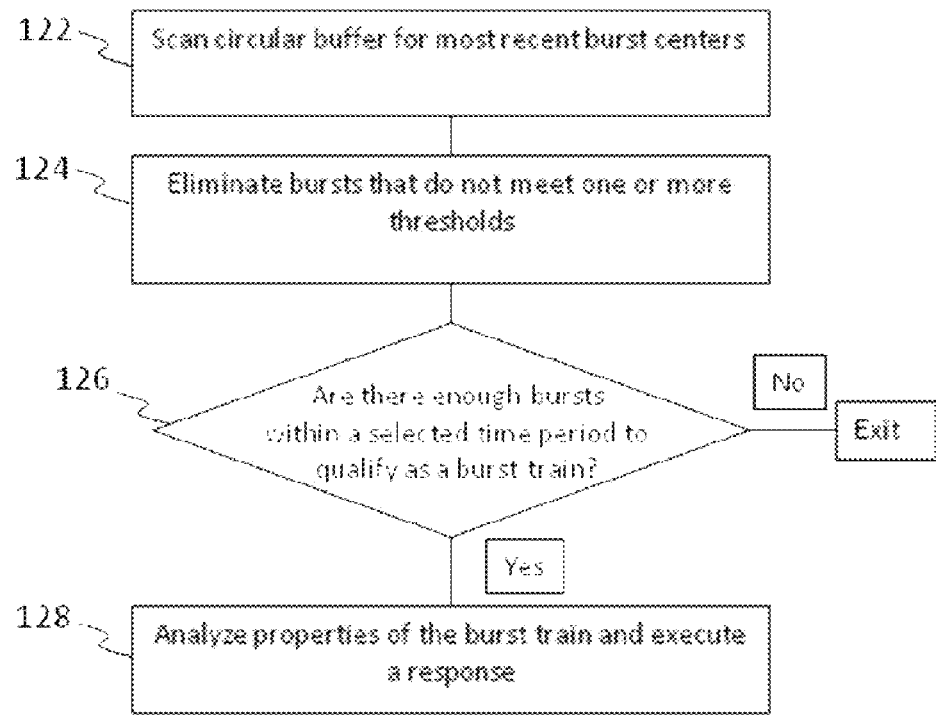
FIG. 9 illustrates an embodiment of a routine for analysis of EMG signal for seizure activity based on detection of a burst train.

FIG. 9 illustrates an embodiment of a burst train detection routine 120 suitable for selection and/or processing of EMG burst train data. The burst train detection routine 120 may, for example, be used in combination with either or both of the routines 72 and 96.

Figure 10:
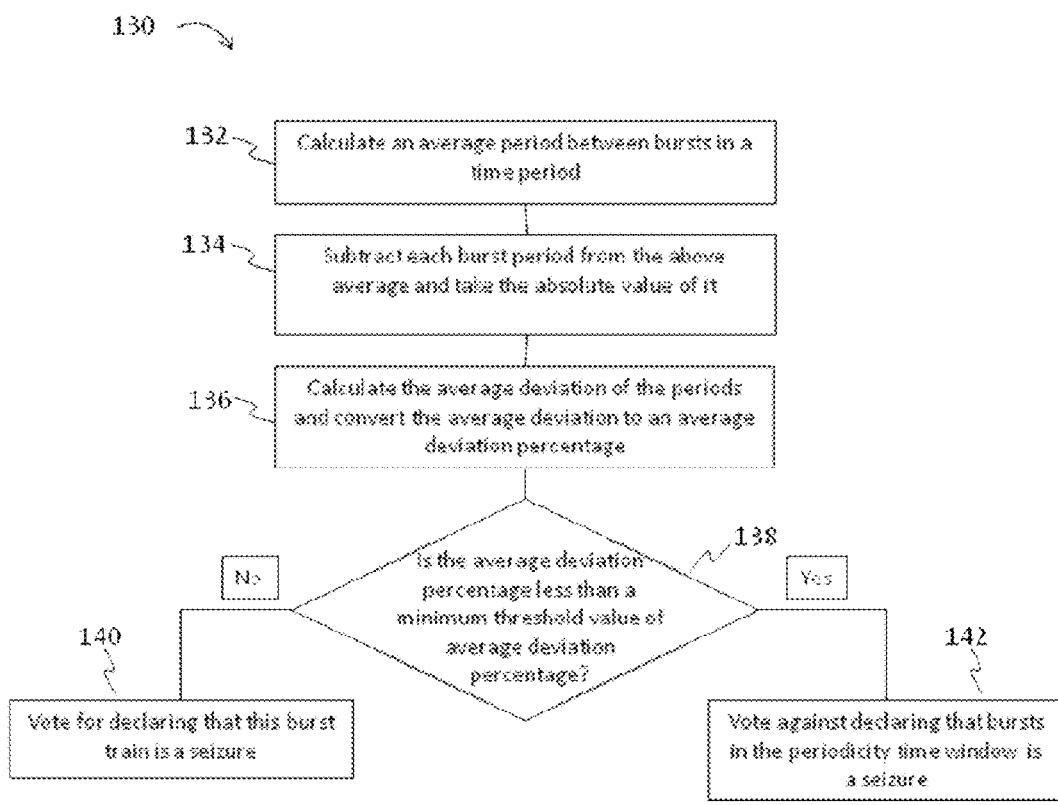
FIG. 10 illustrates an embodiment of a routine for analysis of EMG signal for seizure activity based on detection of burst periodicity.

In a step 122 of the burst train detection routine 120, the routine may scan a circular buffer of data which may store information related to bursts such as may have been detected in the above routines 72 and 96. In some embodiments, scanning of the circular buffer may be initiated at predetermined intervals such as may be set based on a clock routine. In other embodiments, scanning may be initiated based on a trigger signal. For example, each time that data is input into the buffer, such as may occur each time one of routines 72 and/or 96 sends qualified data to the buffer, scanning may be initiated. As indicated in the step 124, in some embodiments, the method 120 may evaluate whether the data in the circular buffer meets one or more threshold conditions. For example, in the step 124, the method 120 may eliminate bursts that are too close together or too far apart from consideration. As indicated in the step 126, the method 120 may determine if a suitable number of bursts are selected to qualify as a burst train. For example, a number of bursts suitable to qualify as a burst train may be about 3 to 20 bursts. More generally, a suitable number of bursts may be selected to generate statistics and/or to look at trends in the signal during the course of a seizure's progression. For example, multiple burst trains may also be analyzed and changes in data between adjacent burst trains may also be calculated. In some embodiments, burst or burst train information may be collected even after an alarm may be initiated. For example, the length of time between bursts may be used to model or track a seizure's progression and may provide valuable information to caregivers. That information may also be used by other devices or sensors such as those used to treat a seizure or that may be used to collect physiological data for a patient. In the step 128, properties of a detected bust train may be analyzed for one or more characteristics that may be indicative of a seizure or seizure related event and an appropriate response may be executed. The step 128 may, for example, include analysis of properties of a burst train such as may be accomplished, for example, using steps or elements in the routine 130 as shown in FIG. 10. By way of further example, a response may be to input a value into a supervisory algorithm that may then be used in determining whether a seizure is detected. In addition, the routine 120 may be used to qualify a possible clonic-phase burst train as a clonic-phase burst train, and the presence of a detected clonic-phase burst train may then be used, for example, to initiate an alarm.

In some embodiments, it may be useful to detect one or more burst trains and determine whether a burst train is indicative of a seizure. For example, a burst train may, for example, be analyzed using one or more routines that determine the periodicity of bursts, regularity of bursts or both. For example, for some patients, bursts may be characterized by some natural variation between individual bursts, and if data is characterized by a burst periodicity that is too low it may be deemed that the data is not likely to be indicative of an actual seizure. Moreover, for many patients, as a seizure progresses quiet time periods between bursts may increase during the seizure. Therefore, bursts may be evaluated over one or more time periods, and if the periodicity of bursts increases over time confidence that the burst data is indicative of a seizure may increase. A burst train may be compared to one or more threshold values related to a characteristic of the bursts, and if a threshold condition is met the burst train may be deemed to be indicative of a seizure. Threshold conditions may be based on data obtained from a patient experiencing a clonic-phase seizure or may be based on clonic-phase data from a patient demographic. Therefore, burst trains may be qualified burst trains and bursts within the train may be qualified to be clonic-phase bursts. In some embodiments, a burst train may be weighted with a value that is not only related to detection of the burst train but also related to the certainty of burst train detection.

As described herein, it may be beneficial to evaluate bursts over an extended period because confidence that the seizure is present and of a certain type or severity may be increased with statistics from longer time periods. However, as also described herein, it may be beneficial to detect a seizure as quickly as possible. In light of those criteria, in some embodiments, particularly if pre-clonic detection of seizures has been made only recently, then it may be useful to wait a certain duration following initial burst detection before initiating an alarm. For example, as long as motor manifestations have only been present for about 15 to about 30 seconds (or some other suitable time period) then a method may collect further burst data and increase confidence of seizure type and/or severity prior to initiating an alarm. And, in some of those embodiments, a periodicity algorithm or other algorithms to calculate bursts statistics may be particularly useful because, for example, a large number of burst may be measured and if those bursts meet qualifications for periodicity such may be highly characteristic of a seizure. Moreover, that data may, for some patients, be gathered and may be diagnostic of risk assessment, and may, for example, be related, at least in some patients, to future CNS depression. Such embodiments may be tailored to specific patients needs, and for some patients, an emergency alarm may be executed as soon as seizure or clonic-phase activity of a seizure is detected.

FIG. 10 illustrates an embodiment of a routine 130 that may be used to characterize the periodicity of bursts and evaluate whether bursts may be indicative of a seizure or stage of a seizure and/or whether the burst should suitably counted in a burst detection routine. The periodicity routine 130 may, for example, look at a circular buffer or register that may store EMG data identified as including qualified or prequalified burst data, and examine, for a selected or determined time period, how regular periods between bursts were. A periodicity routine may scan different data values from various time windows that the burst detection algorithm wrote into a circular buffer, and examine the periodicity of signal characteristics, including those that may not be indicative of a seizure.

In the step 132, of the exemplary method 130 of FIG. 10, an average duration of the periods between bursts within a time period may be calculated. In step 134, individual durations of periods between bursts may be subtracted from the average duration, and the absolute values of the differences used, in step 136, to calculate the average deviation of the periods. In this example, the average deviation may be converted to a percentage although other suitable metrics may be used to characterize variation between periods.

In step 138, the aforementioned percentage (or average deviation percentage) may be compared to threshold values. Such threshold values may be taught to the system in operation and may be customized for a particular patient.

For example, if in a time period (measuring in seconds), nine bursts were detected at the following times:

12, 13, 13.75, 14.35, 15, 15.8, 16.2, 16.5, 17.4 there would be 8 time periods between bursts. So, over a time period including the foregoing epoch of 5.4 seconds, there were nine bursts with eight periods between bursts. The average period may be calculated as $5.4/8=0.675$ seconds per burst. The time periods between bursts are as follows:

$13-12=1$ $13.75-13=0.75$ $14.35-13.75=0.6$ $15-14.35=0.65$ $15.8-15=0.8$ $16.2-15.8=0.4$ $16.5-16.2=0.3$ $17.4-16.5=0.9$

In this example, a simplified method allows the time around which a burst is centered to serve as a time stamp for that burst. In other words, each time the burst algorithm qualifies a burst, a time stamp may be written into a circular buffer for use by the periodicity algorithm. In other embodiments, real burst width may be used to calculate the actual length of the time periods between bursts. For example, if the burst occurring at 12 seconds lasted for 0.02 seconds, then the time period between the burst starting at 12 and the burst starting at 13 would be 0.98 seconds. The absolute value of the deviations from the average may be calculated as follows:

$|1.0-0.675|=0.325$ $|0.75-0.675|=0.075$ $|0.6-0.675|=0.075$ $|0.65-0.675|=0.025$ $|0.8-0.675|=0.125$ $|0.4-0.675|=0.275$ $|0.3-0.675|=0.375$ $|0.9-0.675|=0.225$

Averaging the absolute values may be accomplished as follows:

Sum of all deviations:

0.325+0.075+0.075+0.025+0.125+0.275+0.375+ 0.225=1.5

Average deviation: 1.5/8=0.1875

The average deviation percentage of this average is: 0.1875/0.675=27.8%. That is a significant deviation from the average and may be deemed unlikely to be artificial. For example, a threshold value of average deviation percentage may be set, for example, to 15%, and then the periodicity algorithm may declare that it is likely that the data may be characteristic of a seizure. For example, as shown in the steps 138 and 140, a system would not vote against declaring a seizure. The result may, for example, be placed in a register for use by the supervisory algorithm and may vote for declaring an alarm. Additionally, if the method 130 were applied to qualify bursts, then the method may support a finding that the bursts were related to a seizure, the bursts may then be deemed appropriate for being counted and used to support a positive response in a burst detection routine.

In another simplified example, the burst train may look like this (in seconds):

17, 17.5, 18.02, 18.51, 19.04, 19.56, 20.1, 20.6, 21.13

So, over a periodicity time window including the foregoing epoch of 4.13 seconds, there were nine bursts with eight periods between bursts. The average period may be calculated as 4.13/8=0.51625 seconds per burst. The individual times between bursts are as follows:

17.5−17=0.5

18.02−17.5=4.52

18.51−18.02=0.49

19.04−18.51−0.53

19.56−19.04=0.52

20.1−19.56=0.45

20.6−20.1−=0.5

21.13−20.6−0.53

The absolute value of the deviations from the average may then be determined as follows:

|0.5−0.51625|=0.01625

|0.52−0.51625|=0.00375

|0.49−0.51625|=0.02625

|0.53−0.51625|=0.01375

|0.52−0.51625|=0.00375

|0.45−0.51625|=0.06625

|0.5−0.51625|=0.01625

|0.53−0.51625|=0.01375

The sum of all deviations may be calculated as follows:

0.01625+0.00375+0.02625+0.01375+0.00375+ 0.06625+0.01625+0.01375=1.6

The average deviation is therefore: 1.6/8=0.02.

The percentage deviation of this average is thus: 0.02/0.51625=3.87%. This example thus shows a very regular pattern. If, for example, a threshold value of average deviation were set to 15%, then the algorithm would declare that confidence is very low that a true seizure is occurring and would vote against declaring a seizure alarm (step 142). The result may be placed in a register for use by a supervisory algorithm. Likewise, if the method 130 were applied to qualify bursts, then the method may support a finding that the bursts were not related to a seizure, the bursts may then be deemed inappropriate for being counted and not used to support a positive response in a burst detection routine. Of course, standard deviation calculations or other appropriate metrics related to variability may be substituted for average deviation calculations. Also the thresholds may be derived from the particular patient, averaged model values, or some other method. These thresholds may be variables in the detection unit and may be changed when appropriate.

In some embodiments, data may be automatically formatted and presented for review in a manner suitable to display a determined risk value. For example, in some embodiments. EMG data may be sent and qualified or marked as only corresponding to a warning event. That is, the data may be risk stratified and designated with a non-emergency or warning status. To identify EMG data as associated with a warning or non-emergency status, the EMG data may, for example, be marked with an appropriate status indicator. For example, graphical data may be displayed in a color, font, or with some other marking that identifies the status of the data as only being associated with a warning. Likewise, emergency data may be suitably marked such as in a different color, font, or other marking.

While some caregivers may prefer (or prefer for some patients) that they are immediately notified and sent EMG data for warning events, for other caregivers or for other patients such notification may not be preferred. And, in some embodiments, marking of an event as associated with a warning status may include instructions to buffer the data, e.g., store the data in memory in a caregiver's computer, without actively displaying or notifying the caregiver. And, in some embodiments, a system may include installing instructions in a caregiver or other designated individual's device such as by installing a smart client application to facilitate organization of incoming data. For example, information may, in some embodiments, or with some device settings, be transmitted to a computer but not presented to the user until, for example, corroboration is made that the event demands an emergency response. In the event that the data is corroborated a signal may be sent from a patient detection device (or base station) to update the event status. And, for example, data stored "silently" on a caregiver's computer, may then be rapidly displayed based on an update signal which may only include instructions to update status and may be of minimal data amount. Such embodiments, may, for example, be particularly useful where a caregiver may be at a location where connectivity is intermittent and where data transfer may be limited. In those cases, it may be difficult to send large amounts of data rapidly and sending large amounts of data only after emergency verification may not be desirable or timely.

Data transmitted from a monitoring system, may, in some embodiments, be customized for a particular individual or recipient group. For example, transmitted data may include, an alarm message, subset of statistical information related to algorithm detection, time or frequency domain EMG data, or combinations thereof. For example, in some embodiments, a detection unit may execute as part of a burst detection routine one or more peak detection programs. The burst detection routine may be configured to identify whether one or more bursts of data are present as may be used to determine that a clonic-phase portion of a seizure is present. The burst detection routine, therefore, may be ideally suited for risk stratification and automatic classification of detected event data. And, as part of organizing the EMG data for transmission, a burst statistics window may be provided for presentation of data to a caregiver. The burst statistics window may, for example, include a summary of statistical information regarding a detected pattern of bursts. By way of example only, data that may be included in a burst statistics window include number of detected bursts, rate of burst detection, average signal-to-noise ratio (SNR) of detected bursts, spread of SNR of detected bursts, average width for detected bursts, spread of widths for detected burst, average length of periods between detected bursts, spread of length of periods between detected bursts, deviation of bursts over any number of burst trains, frequency characteristics of burst data, and combinations thereof.

More generally, depending, for example, on a particular routine or set of routines used for seizure event detection, analysis information organized together with other processed or unprocessed EMG data (e.g., data for reconstructing a raw EMG data file) may include a summary of data useful to a caregiver showing what triggered the transmission. That is, organization of transmitted data may include a summary of information to readily communicate to the caregiver why the particular EMG data was selected, and for example, portions of data where a positive response was made for a routine may be identified. And, for example, an output summary of individual detection routines may be presented including threshold setting for the routine and/or certainty values for meeting a given threshold event. By way of nonlimiting example, some of the routines described herein may include analysis of EMG data for sustained amplitude elevations, transient EMG elevations or bursts, and spectral isolation of the EMG data, and depending on what seizure characteristics were deemed to be present associated information may be organized for presentation.

In some embodiments, transmitted data may include EMG data and/or one or more other pieces of data. For example, in some embodiments, a detection unit may further include one or more microelectromechanical inertial detection elements, e.g., gyroscopes, magnetometers and/or accelerometers, that may be configured to determine an orientation of the detection unit and therefore of the muscle upon which the detection unit is attached. Therefore, the system herein may, for example, include a description of whether a sensor (and therefore the muscle to which the sensor may be coupled or attached) was oriented in one way or another. For example, whether the detection unit was oriented substantially vertically, e.g., parallel to a normal vector from the ground as common for a patient standing, or show whether the sensor was oriented horizontal to that normal, e.g., perpendicular to that normal vector, as may be common when a patient is lying such as in bed. Other information that may be organized together with EMG data may include other sensor data such as may be associated with measurement of oxygen saturation in the blood. That information may, in some embodiments, be used to further classify an event, e.g., to further influence a determined risk stratification. And, that information may be used together with EMG data to designate an event as either an emergency or warning event. In addition, in some embodiments, a pulsed oximeter may also be used to monitor a patient and may also be included with a detection device. In some embodiments, risk stratification may further include separate analysis of a patient risk from falling and/or a patient risk of SUDEP. And, each of those may be related to a patient state. For example, whether a patient may be sleeping, home alone, or home alone with another patient. By way of example only, if the patient is sleeping a template file may automatically assign a low risk assessment from falling, but may not adjust a risk of SUDEP.

In some embodiments, organization of information for transmission may include tailoring data transmittal as appropriate for different designated individuals including caregivers, friends, and family. For example, whereas transmittal of data suitable to display either or both of the time and/or spectral dependence of EMG data as well as summary of key analysis features may be transmitted to a particular caregiver, that information may be unnecessary or detrimental if sent to some friends and family. And, in some embodiments, organization of information for transmission may be determined by profiles or settings appropriate for the receiver. For example, friends and/or family may be informed that an emergency alarm or warning was sent, but may not receive raw or processed data suitable to reproduce the time and/or spectral dependence of EMG data or other aspects of data analysis. And, in some embodiments, information may be sent to one group of caregivers who are trained to access from detailed data key seizure characteristics such as, by way of nonlimiting example, whether a particular phase of a seizure is present, various aspects of seizure semiology, and/or orientation data from a microelectromechanical sensor element. Information may also be sent to other caregivers, including some caregivers involved in the emergency response, who may not have different specific training in EMG signal interpretation and may only be sent, for example, information about whether an emergency response is warranted or other sensor data for which they are trained to interpret.

Data selected and organized for transmission may be sent and received by one or more caregivers or other designated individuals. As described above, in some embodiments, EMG or other sensor data may be sent from either or both of a detection unit 12, base station 14, or alert transceiver 16. And, any of the devices 12, 14, and 16, may, as shown in FIG. 1, communicate information to a device for a designated individual. In some embodiments, information may also or alternatively be communicated directly to a caregiver or other designated individual over a local network such as WiFi.

In some embodiments, a caregiver's device may, in some embodiments, include in hardware or software one or more installed programs or set of instructions to facilitate communication and organization of signal data from a transmitting device. And, in some embodiments, instructions for executing one or more routines may be executed using one or more smart client applications. Instructions for updating a status of a detected event may, for example, be included in a caregiver's device and intelligently updated based one or more signals or update signals. Also, instructions for performing any of various routines including those that may be executed by either of a detection unit 12 or base station 14 may also be included in an application on a caregiver's device. And, a caregiver may, for example, be able to vary threshold settings and/or manually adjust thresholds or other routine settings as may be used to further access EMG and/or other data provided from a detection unit 12 or base station 14.

Figure 11:
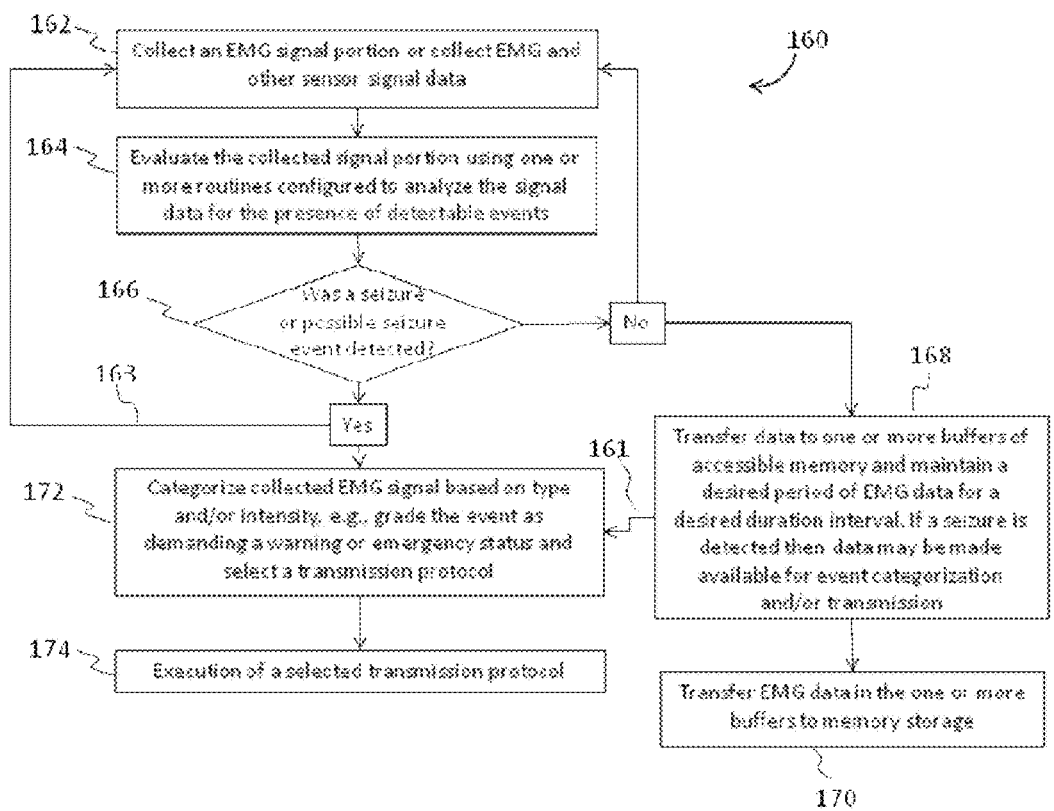
FIG. 11 illustrates another embodiment of a method for monitoring a patient for seizure related activity and selecting a protocol for alarm transmission.

FIG. 11 illustrates another exemplary embodiment of a method 160 of collecting EMG signals and transmitting selected EMG signal data to monitor a patient for seizure activity. In the step 162, a portion of EMG signal or, in some embodiments, EMG signal and other sensor data may be collected. For example, in some embodiments, EMG signals may be collected together with either or both of oximeter data and/or data from one or more orientation and/or position sensitive devices.

In the step 164, collected data may be analyzed using one or more routines configured to determine whether one or more events were detected. At least one routine may, as described above, be selective for a particular portion of a seizure, and if that portion is more or less associated with adverse consequences of a possible seizure, risk stratification may then be facilitated. In the step 166, a decision may be made, e.g., based on any number of EMG analysis routines and/or other information, whether a seizure event was detected. Individual routines may be configured to be selective for a given part of a seizure. For example, in some embodiments, a first routine may analyze collected data for the presence of sustained EMG amplitude and a second routine may analyze collected data for the presence of transient elevations of activity or bursts activity that may be selectively present when a patient experiences a clonic phase of a seizure. And, in some embodiments, an event may be determined using a supervisory algorithm. A supervisory algorithm may, for example, execute a number of sub-routines that combine, such as by appropriately weighting, contributions of various seizure variables in a routine for determining the likelihood that a seizure may be occurring. And, for example, by adjusting a contribution from one or more burst detection sub-routines a routine that includes a supervisory algorithm may be a selective routine. In some embodiments, other sensor data may be integrated with EMG sensor data during the step 164. For example, position and/or orientation data may, in some embodiments, be provided by a detection unit or by a detection unit in combination with a base station and/or environmental transceiver.

And, in some embodiments, a system may, for example, be aware that a patient is likely to be at one location, such as in bed, or at some other location, such as in a bathroom. A system may then, for example, apply different routines and/or routine settings to determine the likelihood that a patient may be having a seizure or engaged in some other activity such as non-seizure moving as dependent upon the location of the user. And, in some embodiments, as described, in Applicant's Provisional Application No. 61/979,225, settings or thresholds may depend upon whether a detection unit may be oriented horizontally or vertically. That is, the system may be particularly calibrated for whether a muscle of a patient is in a certain orientation. And may, for example, be particularly calibrated based on whether a patient may be lying horizontally, lying horizontally with the patient's weight on the sensor, or oriented vertically. In some embodiments, a monitoring system may be configured to enable a patient to update their status based on one more selectable profiles. For example, a patient may be given an option to select one or more different monitoring settings based, for example, on whether the patient is in bed sleeping, whether the patient is at home alone, or if the patient is at home with another person. And, depending on whether the patient selects one of those options the system may select different settings and/or thresholds. Furthermore, for a certain response or group of responses, a monitoring system may, for example, select a transmission protocol associated with either a warning of emergency status that depends on a selected option.

Any of the various routines described herein or, for example, in Applicant's Provisional Application No. 61/969,660 may be executed in order to determine if events are present in the collected EMG signal (steps 164) and then determine whether a seizure was detected (step 166). For example, bursts may be qualified based on fulfilling of a minimum burst width and/or maximum burst width criterion, and if some number of bursts is detected over some period of time a seizure event or possible seizure event may be detected. For example, a burst routine may show a positive response if between about 2 to about 6 bursts are measured within a time window of about 1 second or if another suitable number of bursts are counted in some other appropriate time window. In some embodiments, burst routine may show a positive response if at least about 2 to about 6 bursts are measured within a time window of about 2 to about 5 seconds. And, for example, based on a positive response in a burst routine a seizure may be detected.

As shown in the step 168, data may be transferred and stored in one or more buffers of accessible memory and maintained therein for a desired duration. A next portion of EMG and/or EMG and other signals may then be collected. At the completion of a desired duration interval of EMG signal collection, buffered data may be transferred to another unit of memory, e.g., to permanent memory, as shown in the step 170. More generally, the system 160 may be configured so that transfer of data between one buffer and other storage maintains a suitable portion of data in accessible memory so that the data may be available for transmission if an event is detected. That is, data may be suitably held available if it is deemed necessary for seizure analysis and/or categorization of events or if a transmission protocol is later selected, and that data then included for transmission.

If a seizure or possible seizure event is deemed present, as shown in the step 172, the method 160 may include categorizing the collected EMG signal based on type and/or intensity. And, in some embodiments, the categorized EMG data may then be updated with a status indicator such as a warning or an emergency status. As shown in the method 160 and arrow 161, in some embodiments, one or more portion of data buffered in memory may be accessed when categorizing a seizure. That is, data previously sent to a buffer may be considered, in categorizing a seizure.

In some embodiments, categorization of a seizure may include determining whether one or more routines were responsive to a portion of EMG signal. For example, as shown in Table 1, based on a combination of certain responses to one or more routines a detected event may be categorized. In some embodiments, categorization of a seizure may include accessing data from any combination of an oximeter, orientation sensor, or heart rate sensor. And, for example, in some embodiments, if EMG data may only indicate the presence of a warning event, but either a critical level of saturated oxygen was determined or if the patient's orientation changed from substantially vertical to substantially horizontal an emergency status may instead be determined. For example, risk stratification may be based on either a determination that a patient may have fallen or that a patient shows initial signatures of SUDEP.

In some embodiments, a detected seizure or possible seizure event may be classified based on various metrics, including, by way of nonlimiting example, type, intensity, seizure duration, duration of a seizure phase, other metrics, and combinations thereof. Classification of the severity of a seizure may, for example, include normalizing metrics of the seizure against values typical of a patient or patient demographic. For example, for a patient, if a measured amplitude of a detected characteristic is some factor of a previously measured value for the characteristic (e.g., during another seizure for the patient) or some factor of an average value for the characteristic that factor may be used to grade the seizures severity. That information may, for example, be sent to caregivers and/or otherwise used to determine an appropriate response.

As further described in relation to the step 172, data, including EMG and/or other sensor data, may be selected for transmission. And, a selected protocol may be executed in the step 174. As described above, a decision on whether to select and transmit data may depend upon the categorization of the collected data. And, in some embodiments, a transmission protocol may include instructions to send information to all or only some designated individuals. That is, in some embodiments, an event may be detected and only sent or immediately sent to some caregivers. For example, a routine may identify that a possible seizure was detected, and data may then be sent to one or more remote system users, but not to other designated individuals. The one or more remote system users may, for example, include one or more individuals who are trained to interpret EMG and/or other signals and may be able to corroborate that an actual seizure is occurring using any of various protocols.

For example, a remote user may be able to determine based on the video monitor 9 the condition of the patient. If, for example, video data is not available, the remote user may attempt to contact the patient, e.g., by calling the patient. However, in some cases a remote user may have neither access to video data, may not be able to reach the patient by calling the patient, or may not want to contact the patient in this way. For example, the detected event, or detected event for the particular patient, may be one of only low risk, and it may be likely that the event is a false positive detections. If such occurrences are common for that patient, repeated contact of a patient based on false detection may be a burden and may not be desired. In some embodiments, the user may do further analysis of the data and attempt to conclude if the event is a true emergency, and may thereafter, if the event is not deemed dismissible, attempt to contact the patient and/or update the status of the event. For example, the user may then contact or initiate contact to other designated individuals including other caregivers, friends, and family. Therefore, in some embodiments, and in some situations contact of a caregiver device, e.g., cell phone 17, PDA 18 or other client device, may be mediated through a remote system user.

Generally, the devices of a seizure detection system may be of any suitable type and configuration to accomplish one or more of the methods and goals disclosed herein. For example, a server may comprise one or more computers or programs that respond to commands or requests from one or more other computers or programs, or clients. The client devices may comprise one or more computers or programs that issue commands or requests for service provided by one or more other computers or programs, or servers. The various devices in FIG. 1, e.g., 12, 13, 14, 16, 17, 18 and/or 19, may be servers or clients depending on their function and configuration. Servers and/or clients may variously be or reside on, for example, mainframe computers, desktop computers, PDAs, smartphones (such as Apple's iPhone™, Motorola's Atrix™ 4G, Motorola's Droid™, Samsung's Galaxy S™, Samsung's Galaxy Note™, and Research In Motion's Blackberry™ devices), tablets (such as Sony's Xperia™, Samsung's Galaxy Tab™, and Amazon Kindle™) netbooks, portable computers, portable media players with network communication capabilities (such as Microsoft's Zune HD™ and Apple's iPod Touch™ devices), cameras with network communication capabilities, smartwatches, wearable computers, and the like.

A computer may be any device capable of accepting input, processing the input according to a program, and producing output. A computer may comprise, for example, a processor, memory and network connection capability. Computers may be of a variety of classes, such as supercomputers, mainframes, workstations, microcomputers, PDAs and smartphones, according to the computer's size, speed, cost and abilities. Computers may be stationary or portable, and may be programmed for a variety of functions, such as cellular telephony, media recordation and playback, data transfer, web browsing, data processing, data query, process automation, video conferencing, artificial intelligence, and much more.

A program may comprise any sequence of instructions, such as an algorithm, whether in a form that can be executed by a computer (object code), in a form that can be read by humans (source code), or otherwise. A program may comprise or call one or more data structures and variables. A program may be embodied in hardware or software, or a combination thereof. A program may be created using any suitable programming language, such as C, C++, Java, Per, PHP, Ruby, SQL, and others. Computer software may comprise one or more programs and related data. Examples of computer software include system software (such as operating system software, device drivers and utilities), middleware (such as web servers, data access software and enterprise messaging software), application software (such as databases, video games and media players), firmware (such as device specific software installed on calculators, keyboards and mobile phones), and programming tools (such as debuggers, compilers and text editors).

Memory may comprise any computer-readable medium in which information can be temporarily or permanently stored and retrieved. Examples of memory include various types of RAM and ROM, such as SRAM, DRAM, Z-RAM, flash, optical disks, magnetic tape, punch cards. EEPROM. Memory may be virtualized, and may be provided in, or across one or more devices and/or geographic locations, such as RAID technology. An I/O device may comprise any hardware that can be used to provide information to and/or receive information from a computer. Exemplary I/O devices include disk drives, keyboards, video display screens, mouse pointers, printers, card readers, scanners (such as barcode, fingerprint, iris, QR code, and other types of scanners), RFID devices, tape drives, touch screens, cameras, movement sensors, network cards, storage devices, microphones, audio speakers, styli and transducers, and associated interfaces and drivers.

A network may comprise a cellular network, the Internet, intranet, local area network (LAN), wide area network (WAN), Metropolitan Area Network (MAN), other types of area networks, cable television network, satellite network, telephone network, public networks, private networks, wired or wireless networks, virtual, switched, routed, fully connected, and any combination and subnetwork thereof. The network may use a variety of network devices, such as routers, bridges, switches, hubs, repeaters, converters, receivers, proxies, firewalls, translators and the like. Network connections may be wired or wireless, and may use multiplexers, network interface cards, modems, IDSN terminal adapters, line drivers, and the like. The network may comprise any suitable topology, such as point-to-point, bus, star, tree, mesh, ring and any combination or hybrid thereof.

Wireless technology may take many forms such as person-to-person wireless, person-to stationary receiving device, person-to-a-remote alerting device using one or more of the available wireless technology such as ISM band devices, WiFi, Bluetooth, cell phone SMS, cellular (CDMA2000, WCDMA, etc.), WiMAX, WLAN, and the like.

Communication in and among computers, I/O devices and network devices may be accomplished using a variety of protocols. Protocols may include, for example, signaling, error detection and correction, data formatting and address mapping. For example, protocols may be provided according to the seven-layer Open Systems Interconnection model (OSI model), or the TCP/IP model.

Additional information related to the methods and apparatus described herein may be understood in connection with the examples provided below.

EXAMPLE 1

Figure 12:
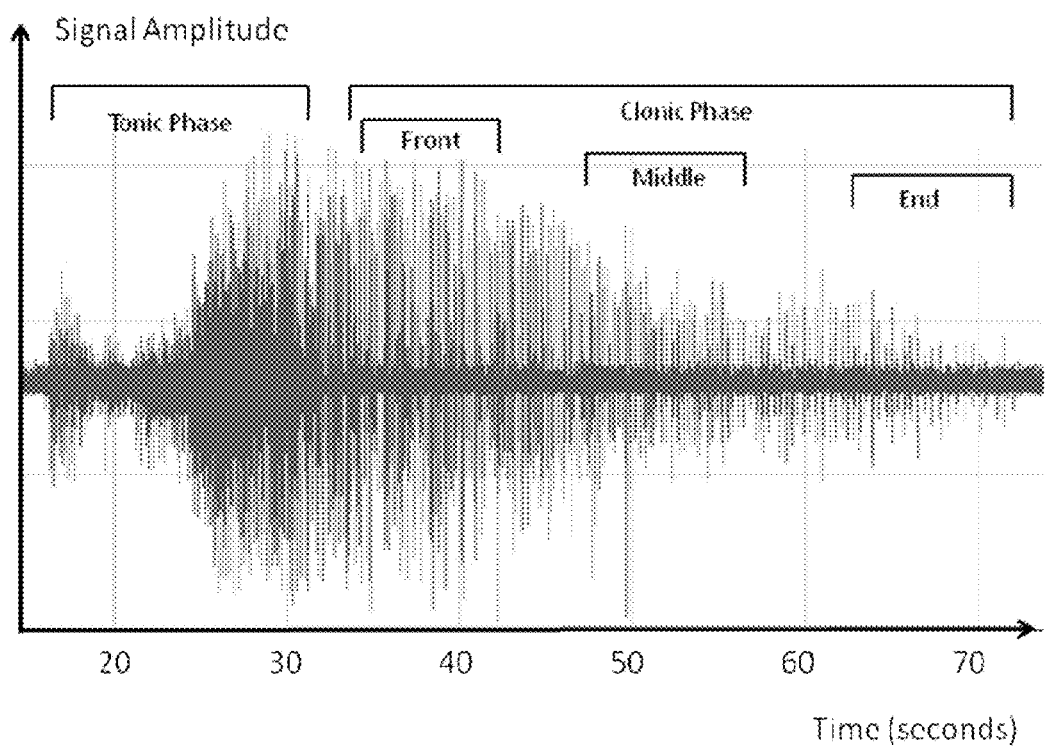
FIG. 12 illustrates EMG signal data.

In this Example 1, a number of patients susceptible to seizures were monitored for seizure activity using EMG electrodes. A sensor was placed on the patient's biceps, EMG signal collected, the collected signal analyzed for the presence of seizure activity, and a seizure was detected. The data herein in this Example 1 includes a summary of 20 different measured seizures from a total of 11 different patients. The seizures and patients herein include a subset of a number of patients in a study to evaluate different methods of seizure detection. And, in each of the 20 seizures in this Example 1, a clonic-phase portion of the seizure was identified. EMG data for one of the recorded seizures is shown in FIG. 12.

EMG data from various portions of the recorded seizures was processed to determine an average period between bursts as well as an average period of burst duration. Burst data was taken from each of several portions of the recorded data. For example, average burst width and average timing between bursts were analyzed during time intervals near the start, intermediate, and later portions of the clonic-phase. Table 2 shows, for the period near the start of the clonic phase, the results for the various patients and seizures in this study.

TABLE 2

| Patient/Seizure Identifier | Time between bursts (sec.) | Burst Width (sec.) |
| --- | --- | --- |
| 1 AcJ | 0.28 | 0.07 |
| 1 ACJ 2 | 0.15 | 0.10 |
| 2 FoB | 0.10 | 0.19 |
| 3 StJ | 0.12 | 0.10 |
| 4 LoJ | 0.22 | 0.21 |
| 5 RiJ | 0.12 | 0.19 |
| 6 MaL | 0.08 | 0.05 |
| 7 MuH | 0.08 | 0.13 |
| 8 WaA | 0.08 | 0.17 |
| 9 PeA1 | 0.11 | 0.11 |
| 9 PeA2 | 0.14 | 0.12 |
| 10 McK1 | 0.14 | 0.12 |
| 10 McK2 | 0.11 | 0.19 |
| 10 McK3 | 0.09 | 0.10 |
| 10 McK5 | 0.11 | 0.11 |
| 10 McK6 | 0.07 | 0.12 |
| 10 McK7 | 0.07 | 0.11 |
| 10 McK8 | 0.08 | 0.07 |
| 10 McK9 | 0.19 | 0.07 |
| 11 ToS | 0.21 | 0.22 |

The average period burst duration at initial parts of the clonic phase for the patients in this study was about 0.12 seconds (or 120 milliseconds). And, by selecting threshold values for minimum burst width of about 25 to about 75 milliseconds and maximum burst width threshold of no greater than about 250 milliseconds to about 400 milliseconds the bursts may be detected. Moreover, other signals that may be present during monitoring, e.g., from non-seizure sources and/or from other phases, did not generally follow this pattern with significant frequency. And, by selecting elevations that meet the aforementioned width requirements bursts may be counted and used to determine whether clonic-activity was present. By detection of clonic-phase activity the seizures may, for example, be differentiated from other seizure events that do not show clonic-phase activity. Furthermore, because clonic-phase activity may be highly indicative of adverse effects of having a seizure the seizures may trigger an appropriate response such as an emergency status.

Additional data for the intermediate and later portions of the clonic-phase is shown in Table 3 intermediate portion) and Table 4 (later portion).

TABLE 3

| Patient and Recorded Seizure | Time between bursts (sec.) | Burst Width (sec). |
| --- | --- | --- |
| 1 AcJ | 0.51 | 0.15 |
| 1 AcJ 2 | 0.20 | 0.08 |
| 2 FoB | 0.26 | 0.18 |
| 3 StJ | 0.18 | 0.13 |
| 4 LoJ | 0.25 | 0.33 |
| 5 RiJ | 0.21 | 0.18 |
| 6 MaL | 0.17 | 0.26 |
| 7 MuH | 0.08 | 0.14 |
| 8 WaA | 0.20 | 0.16 |
| 9 PeA1 | 0.15 | 0.12 |
| 9 PeA2 | 0.17 | 0.12 |
| 10 McK1 | 0.16 | 0.13 |
| 10 McK2 | 0.17 | 0.17 |
| 10 McK3 | 0.16 | 0.10 |
| 10 McK5 | 0.21 | 0.14 |
| 10 McK6 | 0.11 | 0.13 |
| 10 McK7 | 0.10 | 0.10 |
| 10 McK9 | 0.31 | 0.08 |
| 11 ToS | 0.54 | 0.20 |

TABLE 4

| Patient and Recorded Seizure | Time between bursts (sec.) | Burst Width (sec.) |
| --- | --- | --- |
| 1 AcJ | 0.71 | 0.30 |
| 1 AcJ 2 | 0.14 | 0.10 |
| 2 FoB | 0.64 | 0.24 |
| 3 StJ | 0.27 | 0.14 |
| 4 LoJ | 0.49 | 0.33 |
| 5 RiJ | 0.61 | 0.21 |
| 6 MaL | 0.23 | 0.13 |
| 7 MuH | 0.12 | 0.20 |

TABLE 4-continued

| Patient and Recorded Seizure | Time between bursts (sec.) | Burst Width (sec.) |
|---|---|---|
| 8 WaA | 0.29 | 0.17 |
| 9 PeA1 | 0.16 | 0.14 |
| 9 PeA2 | 0.17 | 0.13 |
| 10 McK1 | 0.39 | 0.12 |
| 10 McK2 | 0.13 | 0.18 |
| 10 McK3 | 0.25 | 0.11 |
| 10 McK5 | 0.29 | 0.13 |
| 10 McK6 | 0.14 | 0.12 |
| 10 McK7 | 0.23 | 0.09 |
| 11 ToS | 0.45 | 0.20 |

For some of the monitored seizures, later portions of activity were weak and/or the seizure terminated rapidly. Therefore, in some of the measured seizures only earlier periods of activity were measured. That is, for some of the patients and/or seizures only initial or intermediate portions were measured.

EXAMPLE 2

In this Example 2, a specific embodiment of a method of analyzing collected EMG signals is described. That method may, for example, be used to analyze the seizure data collected above for the patients in the aforementioned study. In Example 2, a first routine may be executed to analyze EMG data for the presence of sustained EMG activity the presence of which may indicate initial motor manifestations of a seizure. A second routine may be executed for the presence of sustained EMG activity, but may include higher thresholds than the first routine. A third routine configured to be selective for clonic-phase activity may also be executed. The responses may be executed simultaneously on a given portion of EMG data. And, in some embodiments, if certain conditions are met a warning period may be initiated.

Table 5 shows, by way of example, some settings that may be applied to monitor the patients in the above study using the first routine of Example 2.

TABLE 5

| Routine Setting | Value |
|---|---|
| Frequency band selected for routine | Full Range/30-55 Hz/ 65-90 Hz/90-120 Hz |
| Threshold EMG level (% of MVC) | 4 |
| Required duration of threshold detection (seconds) | 2 |
| Warning time period setting (seconds) | 20 |

Table 6 shows, by way of example, some settings that may be applied to monitor the patients in the above study using the second routine of Example 2.

| Routine Setting | Value |
|---|---|
| Frequency band selected for routine A | Full Range/30-55 Hz/ 65-90 Hz/90-120 Hz |
| Threshold EMG level (% of MVC) | 50 |
| Required duration of threshold detection (seconds) | 2 |
| Warning time period setting (seconds) | 20 |

Table 7 shows, by way of example, some settings that may be applied to monitor the patients in the above study using the third routine of Example 2.

| Routine Setting | Value |
|---|---|
| Frequency band selected for routine | Full Range/30-55 Hz/ 65-90 Hz/90-120 Hz |
| Threshold SNR (EMG amplitude over background) | 5 |
| Minimum burst duration threshold (milliseconds) | 50 |
| Maximum burst duration threshold (milliseconds) | 300 |
| Threshold burst count rate (Bursts/second) | 2 |
| Qualification routine | Script-X |
| Peak fitting routine | Script-X |

Table 8 shows one embodiment of how a detection of different combinations of the first, second and third routine may be organized.

TABLE 8

| Event | Routine 1 - Status | Routine 2 - Status | Routine 3 - Status | Classification | Status/Transmission Protocol |
|---|---|---|---|---|---|
| A) | Negative | Negative | negative | non-seizure | no transmission |
| B) | Positive | Negative | Negative | possible event | trigger warning period |
| C) | Positive | Positive | Negative | tonic-phase | trigger warning period/ warning transmission protocol |
| D) | positive or negative | positive or negative | Positive | clonic-phase | emergency transmission protocol |

With the routine settings of Example 2, a number of positive responses may be made, and some of those responses may be from non-seizure sources. However, an emergency alarm does not need to be initiated for all combinations of responses. For example, detection may only initiate a warning (that may or may not be provided to an attendant or remote caregiver) and not an emergency response. Or, the system may only trigger a warning period of analysis to some responses, and only after the completion of that warning period may an emergency response be triggered. For example, as shown in Table 8 a warning period of about 20 seconds may be initiated if either the first or second routines are responsive.

If a warning period is triggered as shown, for example, as shown for the events A and B in Table 8, the system may continue capturing EMG data and further classify responses that may be made during the warning period. For example, Table 9 shows one embodiment of how responses to various events (E-H) obtained during a warning period may be considered and possible outcomes to those responses.

| Event | Routine 1 - Status | Routine 2 - Status | Routine 3 - Status | Classification | Status/Transmission Protocol |
|---|---|---|---|---|---|
| E) | Negative | Negative | negative | non-seizure | clear warning flag |
| F) | Positive | Negative | negative | non-seizure | execute recalibration maintain warning flag |
| G) | Positive | Positive | negative | tonic-phase | emergency transmission/ trigger other sensors |
| H) | positive or negative | positive or negative | positive | tonic-clonic seizure | emergency transmission/ trigger other sensors |

For example, if during a warning period routine 2 maintains one or more responses or further responses it may be deemed that an emergency transmission protocol should be executed. Likewise, if the routine 3 shows a positive response within a warning period a tonic-clonic seizure may be likely and an emergency alarm may be executed. In some embodiments, other sensors may be triggered. For example, a pulsed oximeter sensor may be triggered as shown in Table 9. And, for example, if a pulsed oximeter shows that the patient is under further stress, in some embodiments, the emergency response may be adjusted. For example, an emergency transmission may be transmitted to a caregiver, such as a family member or other caregiver who may be in another room of the patient's house. However, if saturated oxygen levels and/or the patient's pulse indicates that the patient is under physiological stress, EMT personnel may be immediately contacted.

Although the disclosed method and apparatus and their advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition, or matter, means, methods and steps described in the specification. Use of the word "include," for example, should be interpreted as the word "comprising" would be, i.e., as open-ended. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods or steps.

What is claimed is:

1. A method of triggering a seizure detection alarm, the method comprising:
   providing a portable EMG detection unit including one or more EMG electrodes and including a portable EMG detection unit processor;
   collecting an EMG signal using said portable EMG detection unit, the portable EMG detection unit configured for executing a first seizure detection routine and a second seizure detection routine;
   executing said first seizure detection routine using said portable EMG detection unit to generate a first output response, said first seizure detection routine configured to be responsive to tonic-phase seizure activity based on detection of a threshold amplitude level of said EMG signal;
   executing said second seizure detection routine using said portable EMG detection unit to generate a second output response, said second seizure detection routine configured to respond selectively to clonic-phase seizure activity based on detection of qualified transient elevations in said EMG signal, said transient elevations being qualified based on a duration of elevation;
   communicating said first output response and said second output response to said portable EMG detection unit processor;
   using said portable EMG detection unit processor for categorizing whether one or more detected events are associated with different types of seizure activity based on whether said one or more detected events are associated with said first output response, said second output response, or a combination of said first output response and said second output response;
   selecting an alarm transmission protocol included among a group of selectable alarm transmission protocols based on said categorizing of said one or more detected events;
   wherein said alarm transmission protocols include sending one or more warning messages or one or more emergency messages, to one or more caregivers;
   said one or more warning messages being configured to inform at least one of said one or more caregivers that a seizure may have occurred;
   said one or more emergency messages being configured to instruct at least one of said one or more caregivers to check on the health status of said patient; and
   executing said alarm transmission protocol.

2. The method of claim 1 wherein said one or more warning messages indicate that said patient is at a low risk of experiencing adverse effects of a detected event.

3. The method of claim 1 wherein said first seizure detection routine is further configured to provide an output in response to muscle motor manifestations that are weaker than typically manifested during tonic-phase seizure activity.

4. The method of claim 1 further comprising providing said patient with an ability to select a selectable status identifier, said selectable status identifier indicating whether the patient is in a selectable patient state.

5. The method of claim 4 wherein said selectable patient state is selected from a patient state indicating that said patient is at home alone, a patient state indicating that said patient is at home in the presence of another person, and a patient state indicating that said patient is sleeping.

6. The method of claim 4 wherein said selecting of said alarm transmission protocol is dependent on said selectable patient state.

7. The method of claim 1 further comprising:
   collecting sensor data using one or more microelectromechanical inertial detection elements configured for determining an orientation of said patient; and
   evaluating a risk of falling for said patient based on said sensor data;

wherein said selecting of said alarm transmission protocol is dependent on said risk of falling.

8. The method of claim 1 further comprising:
collecting sensor data using an oximeter configured to measure levels of saturated oxygen for said patient; and
including said sensor data in an estimate of a risk of said patient experiencing adverse effects of said seizure activity;
wherein said selecting of said alarm transmission protocol is dependent on said estimate of said risk of said patient experiencing adverse effects of said seizure activity.

9. A system for monitoring a patient for seizure activity and executing an alarm, the system comprising:
a portable EMG detection unit including one or more EMG electrodes configured to provide an EMG signal, a portable EMG detection unit processor, and a transceiver;
said portable EMG detection unit processor configured to:
receive said EMG signal;
process said EMG signal to detect one or more events indicating an increased risk of said seizure activity;
analyze said EMG signal using a combination of at least two seizure detection routines configured for the detection of said one or more events;
wherein said at least two seizure detection routines include a first seizure detection routine configured to initiate a positive response to tonic-phase seizure activity based on a detection of a threshold level EMG signal amplitude, and a second seizure detection routine configured to initiate a positive response selectively to clonic-phase seizure activity based on detection of transient elevations in signal qualified based on a duration width;
categorize whether one or more detected events are associated with different types of seizure activity based on whether said one or more events are associated with a response in said first seizure detection routine, a response in said second seizure detection routine, or a response in a combination of said first seizure detection routine and said second seizure detection routine; and
select an alarm transmission protocol included among a group of selectable alarm transmission protocols based on the categorization of said one or more events;
wherein said alarm transmission protocols include sending one or more warning messages, one or more emergency messages, or a combination of both said one or more warning messages and said one or more emergency messages to one or more caregivers;
wherein said one or more warning messages are configured to inform at least one of said one or more caregivers that a seizure may have occurred;
wherein said one or more emergency messages are configured to instruct at least one of said one or more caregivers to check on the health status of said patient; and
said transceiver configured to transmit said one or more warning messages, said one or more emergency messages, or a combination of said one or more warning messages and said one or more emergency messages to a base station or one or more caregivers based on said selected alarm transmission protocol.

10. The system of claim 9 further comprising:
one or more microelectromechanical inertial detection elements configured for determining an orientation of said patient;
wherein said processor is further configured to evaluate a risk of falling for said patient based on data from said one or more microelectromechanical inertial detection elements; and
wherein said selection of said alarm transmission protocol is dependent on said risk of falling.

11. The system of claim 9 further comprising:
one or more oximeters configured to measure levels of saturated oxygen for said patient;
wherein said processor is further configured to include data from said one or more oximeters in an estimate of a risk of said patient experiencing adverse effects of a seizure; and
wherein said selection of said alarm transmission protocol is dependent on said estimate of risk of said patient experiencing adverse effects of a seizure.

* * * * *